(12) United States Patent
Molloy et al.

(10) Patent No.: US 10,993,831 B2
(45) Date of Patent: May 4, 2021

(54) INTEGRAL INLET PORT ASSEMBLY

(71) Applicant: GENTHERM MEDICAL, LLC, Cincinnati, OH (US)

(72) Inventors: Michael Molloy, Cincinnati, OH (US); Brandon Wyatt, Cincinnati, OH (US); Danial Koewler, Batavia, OH (US); Christopher John Mantz, South Euclid, OH (US)

(73) Assignee: Gentherm Medical, LLC, Cincinnati, OH (US)

( * ) Notice: Subject to any disclaimer, the term of this patent is extended or adjusted under 35 U.S.C. 154(b) by 59 days.

(21) Appl. No.: 16/573,012

(22) Filed: Sep. 17, 2019

(65) Prior Publication Data
US 2020/0008976 A1 Jan. 9, 2020

Related U.S. Application Data

(63) Continuation of application No. PCT/US2019/034405, filed on May 29, 2019.

(60) Provisional application No. 62/677,460, filed on May 29, 2018.

(51) Int. Cl.
*F16K 15/20* (2006.01)
*A61F 7/00* (2006.01)
*F16K 1/20* (2006.01)

(52) U.S. Cl.
CPC .......... *A61F 7/0097* (2013.01); *A61F 7/0085* (2013.01); *F16K 1/20* (2013.01); *F16K 1/2042* (2013.01); *A61F 2007/0055* (2013.01); *A61F 2007/0091* (2013.01); *Y10T 137/3584* (2015.04)

(58) Field of Classification Search
CPC .......... Y10T 137/3584; A61F 7/0097
USPC .................. 607/104, 107; 55/367
See application file for complete search history.

(56) References Cited

U.S. PATENT DOCUMENTS

| 625,114 A | 5/1899 | MacSpadden |
| 2,701,579 A | 2/1955 | Hasselquist |
| 2,839,073 A | 6/1958 | Marsh |
| 3,042,941 A | 7/1962 | Marcus |
| 3,432,998 A * | 3/1969 | Downey ............... A47L 9/1454 55/367 |

(Continued)

OTHER PUBLICATIONS

International Search Report and Written Opinion dated Sep. 10, 2019 by the European Patent Office (as International Searching Authority), for related International Application No. PCT/US2019/034405, filed May 29, 2019 (11 pages).

*Primary Examiner* — Robert K Arundale
(74) *Attorney, Agent, or Firm* — The Dobrusin Law Firm, P.C.

(57) ABSTRACT

A unitary inlet port assembly for use as a closable air inlet port for an inflatable heating blanket or garment. The inlet port assembly has a port panel on the outside of blanket, having an inlet opening configured for receiving an air hose nozzle. A closure panel that is disposed within an interior portion of the inflatable heating blanket or garment, and is hinged an edge of the port panel. A latch extends from an outer-facing surface of the closure panel, to register with the inlet opening of the port panel when pivoted to a closed position. At the closed position, the outer-facing surface of the closure panel confronts and engages the inside surface of the port panel to close the air inlet port. The latch is configured to engage the annular rim of the port panel to hold the closure panel in the closed position.

21 Claims, 17 Drawing Sheets

(56) References Cited

U.S. PATENT DOCUMENTS

| | | | | |
|---|---|---|---|---|
| 3,933,451 A * | 1/1976 | Johansson | | A47L 9/1445 |
| | | | | 55/367 |
| 4,258,904 A | 3/1981 | Scremin | | |
| 4,361,249 A | 11/1982 | Tuneski et al. | | |
| 4,395,800 A * | 8/1983 | Shindelaar | | F16L 3/00 |
| | | | | 24/569 |
| 4,572,188 A | 2/1986 | Augustine | | |
| 4,787,875 A | 11/1988 | Baron | | |
| 4,823,831 A | 4/1989 | Jaw | | |
| 5,045,099 A * | 9/1991 | Goldberg | | A47L 9/1445 |
| | | | | 55/367 |
| 5,050,758 A | 9/1991 | Freeman et al. | | |
| 5,119,842 A | 6/1992 | Jaw | | |
| 5,226,941 A * | 7/1993 | Uibel | | A47L 9/1436 |
| | | | | 55/367 |
| 5,379,810 A * | 1/1995 | Marino | | F16L 55/00 |
| | | | | 137/312 |
| 5,405,371 A | 4/1995 | Augustine | | |
| 5,468,271 A * | 11/1995 | Sauer | | A47L 9/1436 |
| | | | | 55/357 |
| 5,997,572 A * | 12/1999 | Arnold | | A61F 7/00 |
| | | | | 138/89 |
| 6,138,711 A | 10/2000 | Lung-Po | | |
| 6,228,107 B1 | 5/2001 | Arnold | | |
| 6,309,408 B1 | 10/2001 | Arnold | | |
| 6,460,560 B1 | 10/2002 | Weinheimer | | |
| 6,666,879 B2 | 12/2003 | Arnold | | |
| 7,658,756 B2 * | 2/2010 | Pierre | | A61F 7/02 |
| | | | | 607/107 |
| 9,371,924 B2 | 6/2016 | Foucault | | |
| 2003/0014821 A1 | 1/2003 | Boyd | | |
| 2003/0037378 A1 | 2/2003 | Wu | | |
| 2005/0125904 A1 | 6/2005 | Tsai | | |
| 2010/0089458 A1 | 4/2010 | Chaffee | | |
| 2010/0094067 A1 | 4/2010 | Kim | | |
| 2010/0206914 A1 | 8/2010 | Doron | | |
| 2011/0022134 A1 * | 1/2011 | Anderson | | A61F 7/0097 |
| | | | | 607/104 |
| 2011/0297247 A1 * | 12/2011 | Deutsch | | A47C 27/081 |
| | | | | 137/233 |
| 2014/0277307 A1 | 9/2014 | Gammons et al. | | |

\* cited by examiner

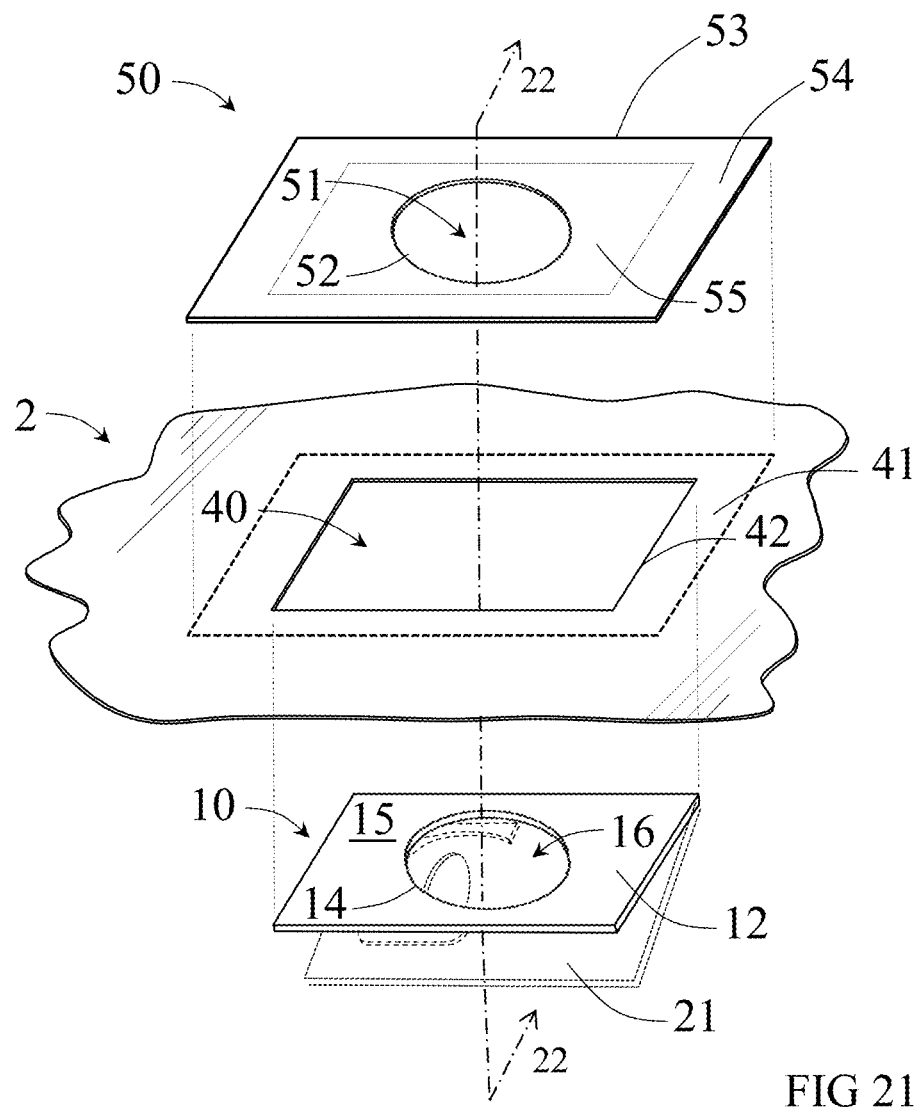
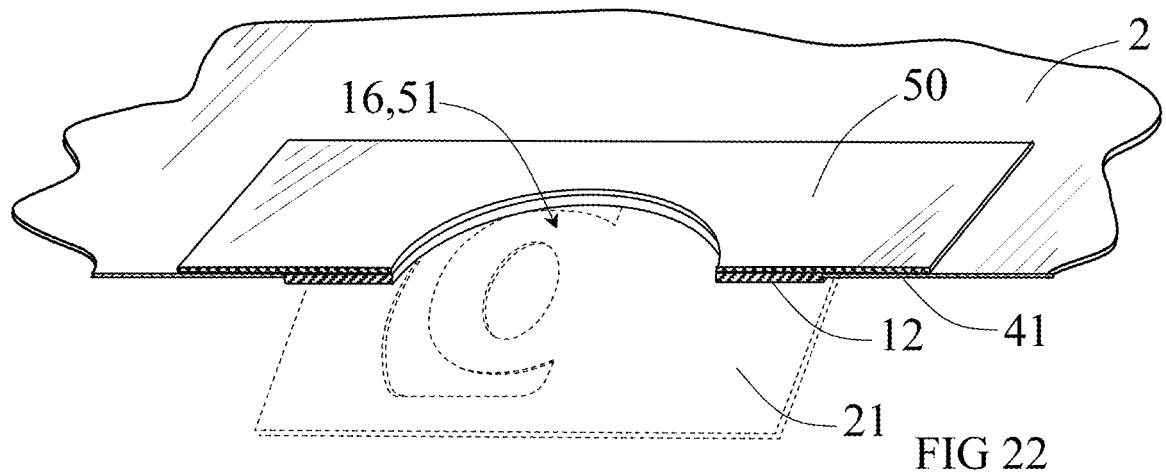

INTEGRAL INLET PORT ASSEMBLY

CROSS-REFERENCE TO RELATED APPLICATIONS

This application is a continuation of International Patent Application No. PCT/US2019/034405, filed May 29, 2019, which claims the benefit of U.S. Provisional Application No. 62/677,460, filed May 29, 2018, which are incorporated herein by reference in their entireties.

BACKGROUND OF THE INVENTION

Field of the Invention

The present invention relates to devices for warming a patient during a medical procedure, and more particularly, to a device for restricting air flow through an inlet port in an inflatable thermal blanket used to warm a patient during a medical procedure.

Description of the Related Art

Hypothermia, a condition in which a person's body temperature drops below normal, presents serious and potential consequences to a patient. Studies have shown that hypothermia occurs in nearly 75 percent of all patients who undergo surgical procedures. Based on recent numbers, this means that 14 million patients a year in the United States alone suffer from hypothermia during surgical procedures. Hypothermia during surgery may be caused by anesthesia, air conditioning within the operating room, infusion of cold blood or IV solutions or irrigation fluids, in addition to other factors.

One well known method for reducing hypothermia during surgical procedures is to place an inflatable thermal blanket over a patient during a surgical procedure. The thermal blanket is inflated with a warmed airstream, exhausting warmed inflating air onto the patient. An inflatable thermal blanket was first disclosed in U.S. Pat. No. 4,572,188 assigned to Augustine Medical, Inc., the assignee of the present application. U.S. Pat. No. 5,405,371, also assigned to Augustine Medical, Inc., is directed to an inflatable thermal blanket that extends transversely across the arms and chest of a patient's body, and is for use during surgery at or below the patient's chest. These patents disclosed an airstream inlet: In later products, the airstream inlet port comprises a cardboard structure adhesively attached to the surface of the thermal blanket. A hole provided through the inlet port is sized to accept the end or nozzle of an inflation hose. In some thermal blankets, a plurality of inlet ports are provided to allow an inflation hose to be attached at any one of a plurality of locations on the blanket. When an operator inserts the inflation hose into an inlet port, the port is closed about the hose. The surface material of the thermal blanket which coincides with the inlet port is either removed or perforated in order to allow a warmed airstream to pass from the hose through the port to the interior of the thermal blanket. The warmed airstream enters the thermal blanket and is forced out a plurality of small exhaust holes in the lower surface of the thermal blanket. Typically, the user perforates or removes that portion of the thermal blanket which covers an inlet port only when that port is to be used. Accordingly, each of the unused inlet arts remains sealed until after the first use.

One problem with this design is that if the operator decides in the middle of the procedure to move the inflation hose from one inlet port to another, the first port must be resealed or otherwise closed in order to prevent air from exiting through that port instead of through the holes on the lower surface of the blanket, as intended. A number of means have been used to reseal or close an inlet port after removal of an inflation hose. However, none of these means are completely satisfactory. For example, tape has been used to seal an open port, but is generally a nuisance to apply. The prior art suggests many other means and modes for sealing or closing an open port, including: adhesive strips, double sided tape, snaps, zippers, folding flaps, Ziplock®-type seal, hook and loop fastener strips, folding wire, or plastic bars. Each of these methods has a number of drawbacks. U.S. Pat. No. 6,666,879 B2 discloses an inlet port plug having a generally planar shape with coplanar extensions extending radially from a plug body. The inlet port plug may be engaged with an inlet port by causing at least two of the extensions to be received in the inlet port. When the extensions are received, the plug is retained against the inlet port. The method is either relatively costly, or it is inconvenient, requiring a great deal of attention or time of an operator, possibly during critical moments. Such methods and means require accommodation in manufacture of a thermal blanket, increasing production costs and decreasing manufacturability. The inlet port plug is a separate element, unattached to the inlet port of the thermal blanket, and may be dropped on the floor or lost during a procedure.

Accordingly, there is a need for an improved inlet air plug that remains attached to or associated with the air inlet port of the thermal blanket, to avoid loss or dropping that can contaminate the inlet port plug.

SUMMARY OF THE INVENTION

This invention provides a unitary inlet port assembly that includes a closure panel attached to or associated with a port panel having an inlet opening, for selectively opening and closing the inlet opening. The inlet port assembly is adapted for mounting on an inflatable device. A non-limiting example of an inflatable device is a patient warming blanket or gown. The port panel comprises a planar sheet of material that is flexible and resilient, having the inlet opening. The inlet opening has a shape and a structure for engaging and retaining an air hose nozzle through which air can pass to inflate the inflatable device. When not engaged by an air hose nozzle, the inlet opening of the port panel can be closed, blocked, or sealed with the closure panel. The closure panel folded into the closed position blocks the inlet opening of the port panel in order to inhibit, restrict or prevent air escaping the inflatable device when being inflated.

In an embodiment of the invention, the unitary inlet port assembly is useful as a closable air inlet port for an inflatable heating blanket or garment. The unitary inlet port assembly includes: a) a port panel associated with an outside layer of the inflatable heating blanket or garment, the port panel including a side edge, an inside surface, and an annular rim defining an inlet opening through the port panel that is configured for receiving an air hose nozzle; and b) a closure panel, disposed within an interior portion of the inflatable heating blanket or garment, the closure panel including an outer-facing surface, and a side edge that forms a panel hinge with the side edge of the port panel. A latch extends from and is positioned on the outer-facing surface, to register with the inlet opening of the port panel when the closure panel is pivoted to a closed position at which the outer-facing surface of the closure panel confronts and engages the inside surface of the port panel. The latch is configured to engage the annular rim of the port panel to hold the closure panel in the closed position.

The closure panel includes generally planar body with an outwardly-facing surface, and a latch affixed to the outwardly-facing surface. The latch can be configured for grasping manually or with an implement or tool, for pulling the outwardly-facing surface of the planar body against an inner surface of the port panel, to close off the inlet opening.

In one embodiment, the port panel and the closure panel can be formed from a unitary panel member that is folded at the hinge. In another embodiment, the port panel and the closure panel can be separate panel materials, that are attached by adhesive, an attaching flap, or a joint material such as tape.

In an embodiment of the invention, the latch is configured to affix or attach to the port panel when folded into the closed position, so that the closure panel remains in the closed position when the user releases the latch. Affixing or attaching of the latch to the port panel can be either a selective or a spontaneous affixment or attachment.

In an embodiment of the invention, the closure panel has a side edge that is joined to a side edge of the port panel, forming a hinge that enables the outwardly-facing surface of the closure panel to pivot away from or into engagement with the inner surface of the port panel.

In another embodiment of the invention, the latch provides a handle for grasping. The latch can comprise a loop or ring of a material that is attached to a portion of the outwardly-facing surface of the closure panel that pivotably registers with the inlet opening of the port panel when the closure panel is pulled to the closed position and into engagement with the port panel. This enables a user to reach through the inlet opening, and grasp and pull the latch through the inlet opening, to a pulled-through position. In the pulled-through position of the latch, the outwardly-facing surface of the closure panel confronts for engagement with the inner surface of the closure panel, in the closed position.

In an embodiment of the invention, the latch includes a means for retaining the latch in a pulled-through position. In a particular embodiment of the invention, the latch is formed from a planar material into a tab having a circular or oval shape. In one embodiment, two opposed lateral portions of the latch that extend laterally beyond the neck to a dimension that is the same, or slightly smaller than, the corresponding diameter or maximum dimension of the inlet opening, allowing the latch to be pulled through the inlet opening of the port panel with little or no resistance with the rim of the inlet opening.

In a further embodiment, the fold line of the neck portion, which attaches the latch to the to the closure panel, extends along a chord line, in the closed position, which is parallel with but offset from a centerline through the diameter or maximum dimension of the inlet opening. With the fold line of the latch positioned along the chord line, the opposing portions a neck of the latch can frictionally engage and wedge against the rim of the inlet opening, to better secure the closure panel in the closed position.

In another embodiment, a lateral dimension of the latch extends wider than, and preferably slightly wider than, the corresponding diameter or maximum dimension of the inlet opening, thereby requiring that the latch be curled around an axis of the latch, to pass the latch through the inlet opening.

In one embodiment, the fold line of the latch is parallel with the panel hinge that joins the port panel with the closure panel. In this embodiment, the latch pivots at the fold line in an arc that is perpendicular to the panel hinge. A line through the fold line, when the closure panel is folded into the closed position, defines a chord line of the inlet opening that is axially off-set from the lateral centerline of the inlet opening.

In another embodiment, the fold line of the latch is perpendicular with the panel hinge, and in this embodiment, the latch pivots at the fold line in an arc that is parallel to the panel hinge. In one embodiment, a line through the fold line, when the closure panel is folded into the closed position, defines a chord line of the inlet opening that is laterally off-set from the axial centerline of the inlet opening. In another embodiment, the line along the fold line aligns with the axial centerline of the inlet opening.

In another embodiment of the invention, the latch material is integral with and an extending portion of the material of the inlet port plug, and extends pivotally from the outwardly-facing surface of the inlet port plug.

In an embodiment of the invention, the port panel is a panel portion of a tubular member that is disposed within a tubular section of the interior portion of the inflatable heating blanket or garment. The tubular member includes at least two additional panels, including a first panel that includes a side edge that forms a second panel hinge with said side edge of the port panel, and a second panel that includes a side edge that forms a third panel hinge with an opposed side edge of the port panel. A third panel can be provided to attach at opposite ends to the second and third panels forms a rectangular tubular port assembly.

BRIEF DESCRIPTION OF THE DRAWINGS

FIGS. 21 and 23 illustrate each a partial, expanded view of a blanket inlet port, showing the outer air-impervious film material having an opening formed for inserting the unitary inlet port assembly, and an adhesive sealing film for securing and sealing the inlet port assembly to the outer air-impervious film material.

FIGS. 22 and 24 show a section view of the blanket inlet ports of FIGS. 21 and 23, respectively, in an assembled blanket.

DETAILED DESCRIPTION OF THE INVENTION

The present invention provides a unitary inlet port assembly having a selectively closable opening, useful with an inflatable thermal blanket, and a method for its use with the inflatable thermal blanket.

Figure 1:
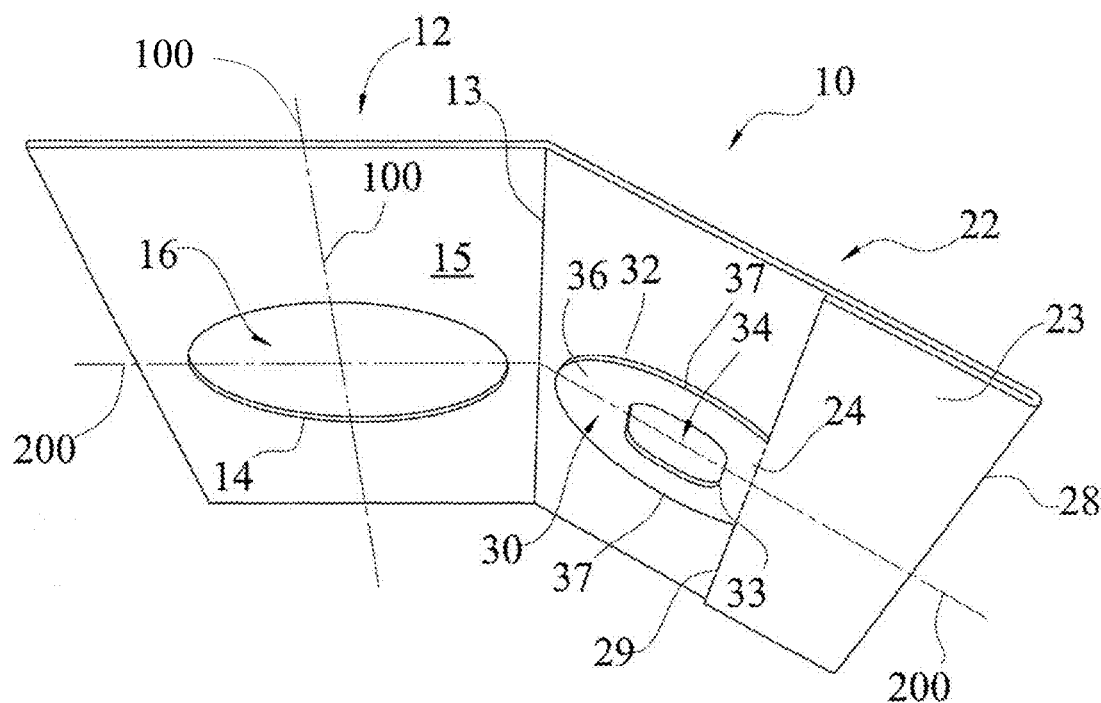
FIG. 1 illustrates an underside view of an embodiment of the present invention of a unitary inlet port assembly that includes a port panel having an inlet opening, hinged to a closure panel having a latch, for selectively securing the closure panel against the inlet opening.
Figure 2:
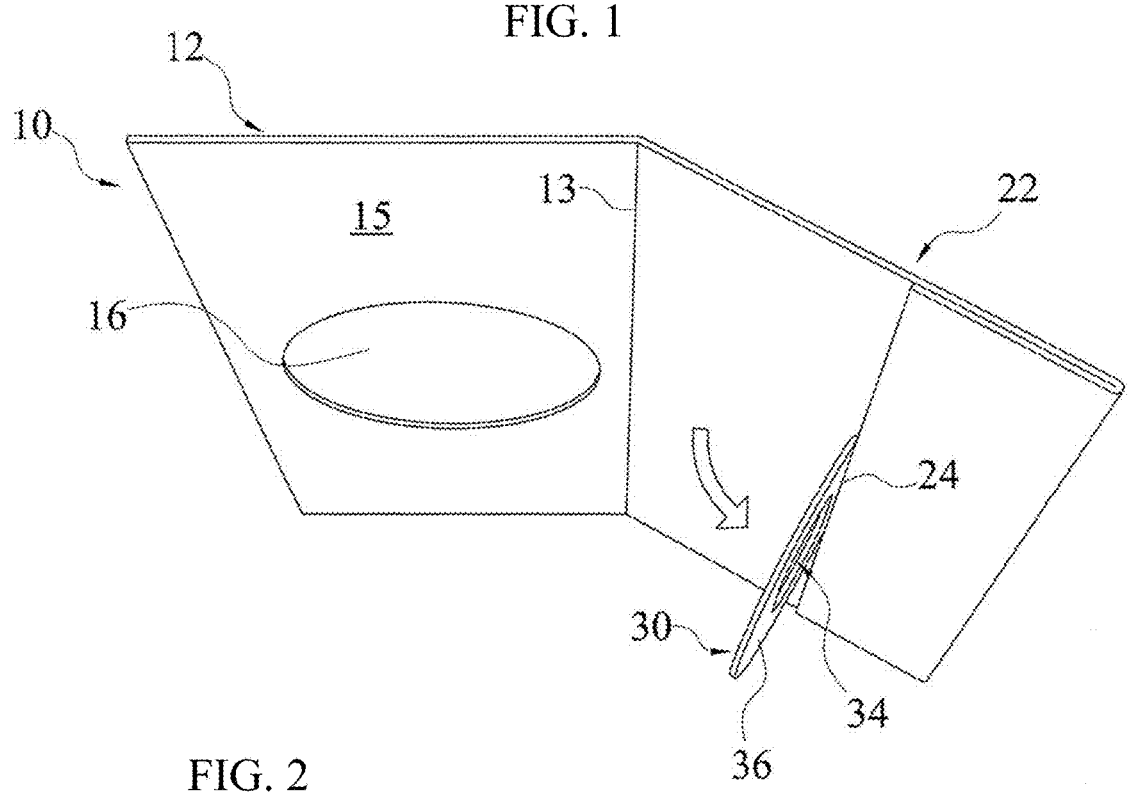
FIG. 2 illustrates the unitary inlet port assembly of FIG. 1 with the latch pivoted away from the closure panel.
Figure 20:
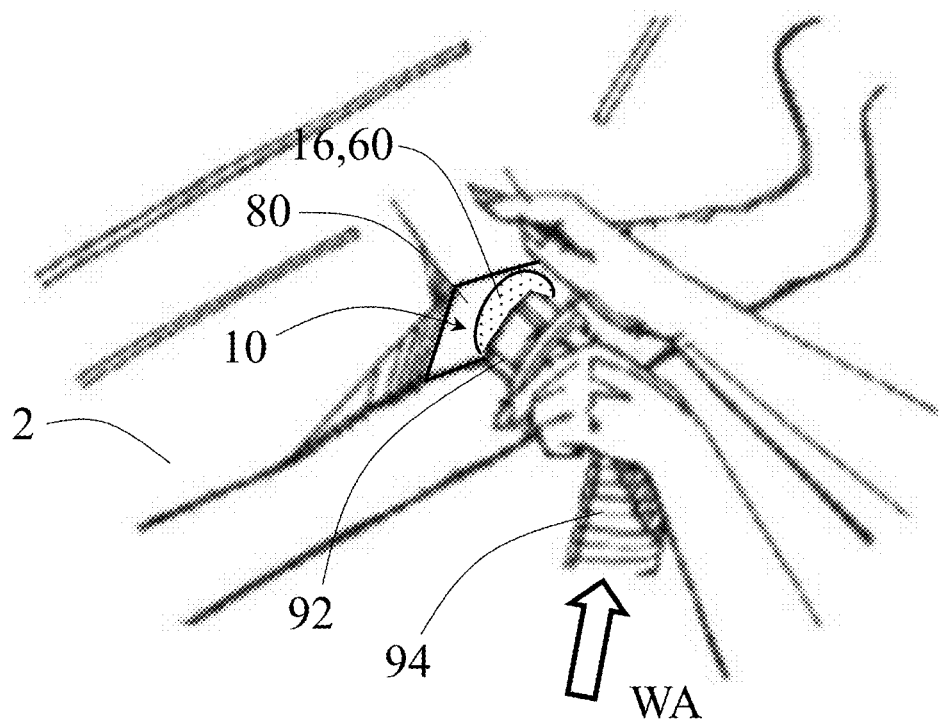
FIG. 20 illustrates a warm air hose being inserted into the inlet opening of the unitary inlet port assembly of a heating blanket by a user to inflate the blanket.

A first embodiment of the present invention is shown in FIGS. 1-8. FIGS. 1 and 2 show the unitary inlet port assembly 10 in an open position. The inlet port assembly 10 includes a port panel 12 and a closure panel 22, with an edge of the closure panel 22 hingedly attached to an edge of the port panel 12 to form a panel hinge 13. The port panel 12 includes an inner face surface 15 that includes a port rim 14 that defines a shaped opening 16 formed through a central portion of the port panel 12. The port panel 12 provides an air inlet port defined by the port rim 14 having a circular shape, to define a shaped, inlet opening 16. In the open position, the closure panel 22 is typically easily pivotable away from, or biased away from, the port panel 12, to ensure the closure panel 22 moves pivotably away when an inlet air nozzle 92 (see FIG. 20) is inserted into the inlet opening 16.

The shaped opening 16 is shown disposed in the panel 12, with its circular shape centered along a lateral centerline 100 and a longitudinal centerline 200. In other embodiments of the invention, the shaped opening 16 can be offset from the lateral centerline 100, or the longitudinal centerline 200, or both, as needed or desired. In other embodiments of the invention, the shaped opening 16 can be non-circular, symmetrical in shape, or non-symmetrical in shape. In one embodiment, the shaped opening 16 can be oval shaped, with the longer axis aligned with either of the lateral centerline 100 or the longitudinal centerline 200.

The closure panel 22 includes a latch 30 attached to the closure panel 22 along a hinge 24. The hinge 24 extends parallel with the panel hinge 13, and is parallel with the lateral centerline 100 when the closure panel 22 is folded against the port panel 12 in a closed position, shown in FIG. 7. The closure panel 22 provides a closure that covers the inlet opening 16 to form a port closure.

The latch 30 includes a tab having a circular or oval shape defined by an outer periphery 32. The outer edge 36 provides a place for a user to grasp the latch 30. A finger hole 34 can be formed in the body of the latch 30 to provide a catch for a finger of the user. The latch 30 includes a neck portion 33 that attaches to the closure panel 22 along the hinge 24, and opposed lateral portions 37 that extend laterally beyond the neck portion 33 and the ends of the hinge 24, and span a distance that is greater than the length of the hinge 24.

Figure 3:
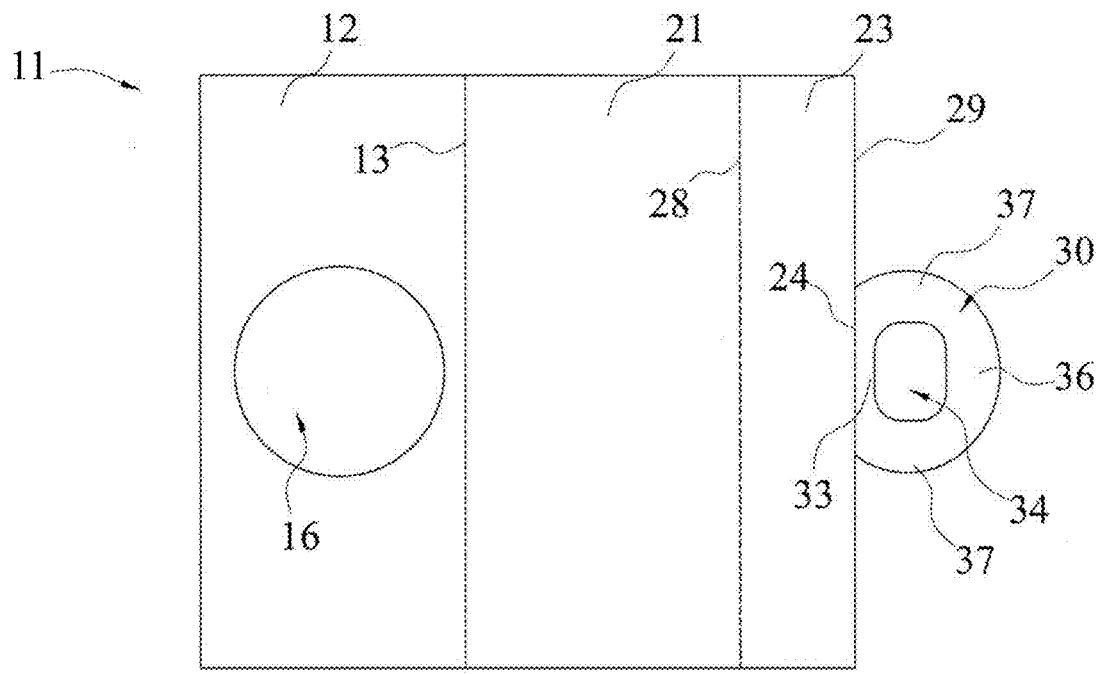
FIG. 3 shows a plan view of a blank used to form the unitary inlet port assembly of FIG. 1.
Figure 4:
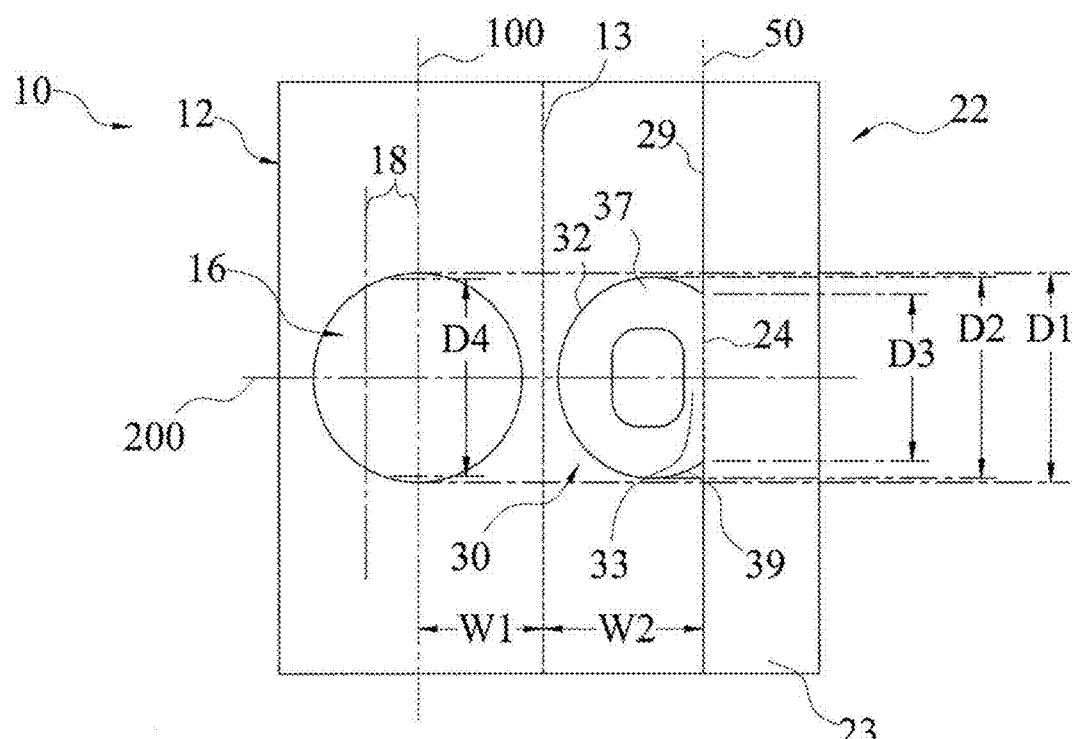
FIG. 4 shows a plan view of the blank of FIG. 3 formed into the unitary inlet port assembly of FIG. 1.

FIGS. 3 and 4 show a plan view of the unitary inlet port assembly 10. FIG. 3 shows a blank 11 that is formed out of a planar material, which forms the unitary inlet port assembly 10 after being folded and fixed as shown in FIG. 4. The blank 11 includes the port panel 12, a closure base 21 having a first side edge attached to a side edge of the port panel 12 along a hinge joint 13, and a second side edge attached to a first edge of a flap panel 23 along a foldable joint 28. In the illustrated embodiment, the flap panel 23 has a second opposed edge 29, and includes the latch 30 attached to the edge 29 along a hinge 24. The flap panel 23 is folded inwardly along the foldable joint 28, and is secured or fixed to the closure base 21 to form the closure panel 22, which is hingedly attached to the port panel 12 along the panel hinge 13.

In FIG. 4, a plan view of the inlet port assembly 10 is shown including the port panel 12 having the inlet opening 16 having an open area having a lateral width D1, and in the illustrated embodiment a largest lateral width D1 along the lateral centerline 100, illustrated as a circle with a diameter D1. On the closure panel 22, the neck 33 joins the latch 30 to the flap panel 23 along the hinge 24 having a length of D3, while the opposed lateral portions 37 or "ears" of the latch 30 have a span of a length of D2, greater than the length D3. In an embodiment, the span length D2 of the ears 37 of the latch 30 is the same or slightly shorter than the largest lateral width D1 along the lateral centerline 100. In another embodiment, the span length D2 of the ears 37 of the latch 30 is slightly larger than the largest lateral width D1 along the lateral centerline 100, and the latch 30 can be elastically deformed or curled slightly along the longitudinal centerline 200 to facilitate passing the ears 37 through the inlet opening 16. Further, the length D3 of the neck 33 is within a length range of a lateral chord length D4 between laterally-opposed portions 19 of the port rim 14 in the region 18.

Figure 7:
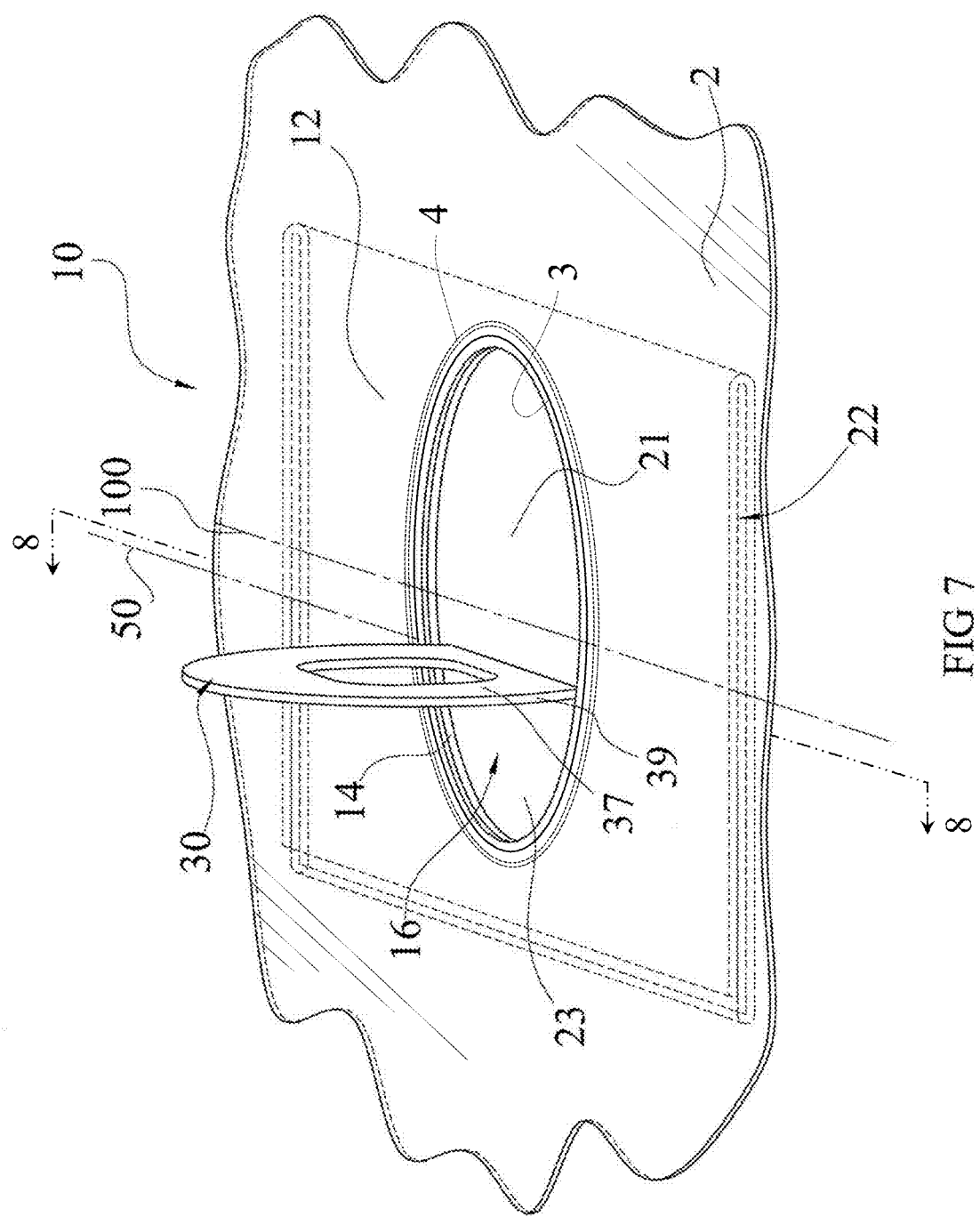
FIG. 7 illustrates a topside view of the inlet port assembly, now installed into a fabric layer of a heating blanket, with the closure panel pulled into a closed position against the inlet port, and the latch pulled through the inlet opening into a secured position against the rim of the inlet opening.

The lateral centerline 100 is disposed at a length W1 from the panel hinge 13 that joins the port panel 12 and the closure panel 22. The closure panel 22 includes the latch 30 joined to the closure panel 22 along the hinge 24, which is co-extensive with the edge 29 of the flap panel 23, and is disposed at a length W2 from the panel hinge 13 in the position shown in FIG. 4. In one embodiment, length W2 is greater than the length W1, so that when closure panel 22 is folded over, the hinge 24 is disposed along a lateral line that lies in the region 18 that defines a transverse chord of the circular inlet opening 16. By offsetting the hinge 24 from the lateral centerline 100 of the inlet opening 16 in the closed position, the lateral portions or "ears" 37 of the latch 30 can still pass with minimal clearance through the lateral center of the inlet opening 16, and when, as shown in FIG. 7, the latch 30 is un-folded on the outer side of the inlet opening 16, the opposing tapered portions 39 of the neck 33 of the latch 30 frictionally engage and wedge against the laterally-opposed portions 19 of the port rim 14 within the region 18, to better secure the closure panel 22 in the closed position.

In an alternative to the first embodiment, a span of the opposed lateral portions 37 of the latch 30 can extend as wide as or wider than the corresponding diameter or maximum dimension of the inlet opening 16. In this embodiment, to pass the latch 30 up and through the inlet opening 16, the user can curl the opposed lateral portions or "ears" 37 around a center axis of the latch 30, to pass the latch 30 through the inlet opening 16. In this alternative embodiment, the hinge 24 of the latch 30 to the closure panel 22 can be positioned to register co-axially with the lateral centerline 100 of the inlet opening 16, in the closed position, though can also be slightly off-set therefrom. This alternative embodiment would require more dexterity from a user, but also provide a secure configuration on the part of the closure panel 22 in the closed position.

Figure 5:
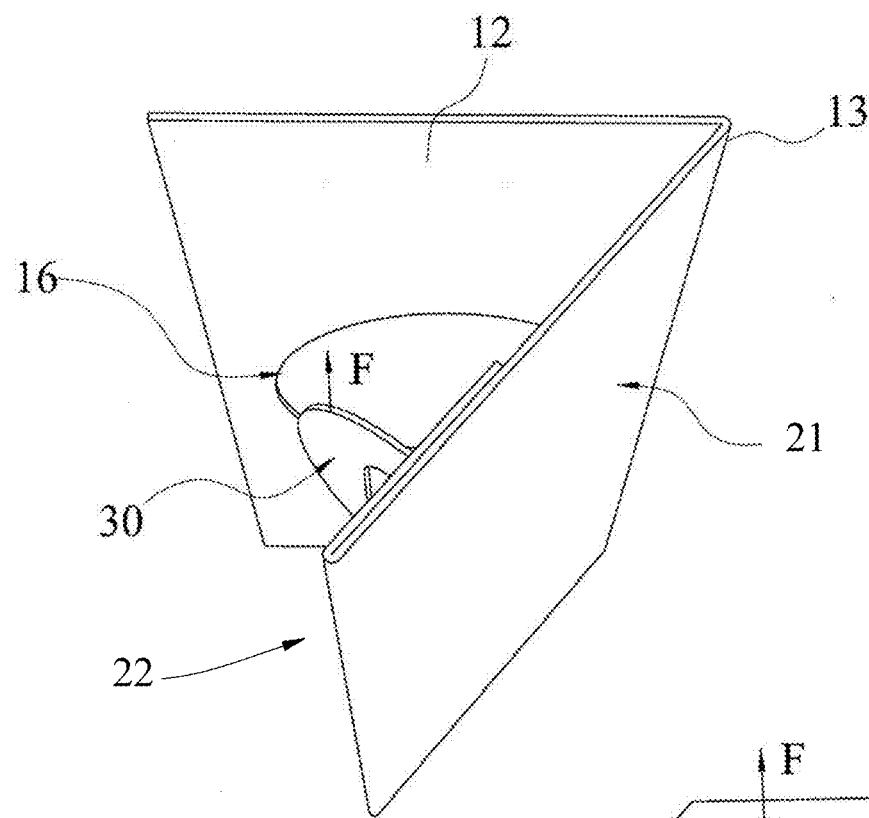
FIG. 5 illustrates an underside view of the inlet port assembly of FIG. 2 with the closure panel pivoting toward the inlet opening of the port panel.
Figure 6:
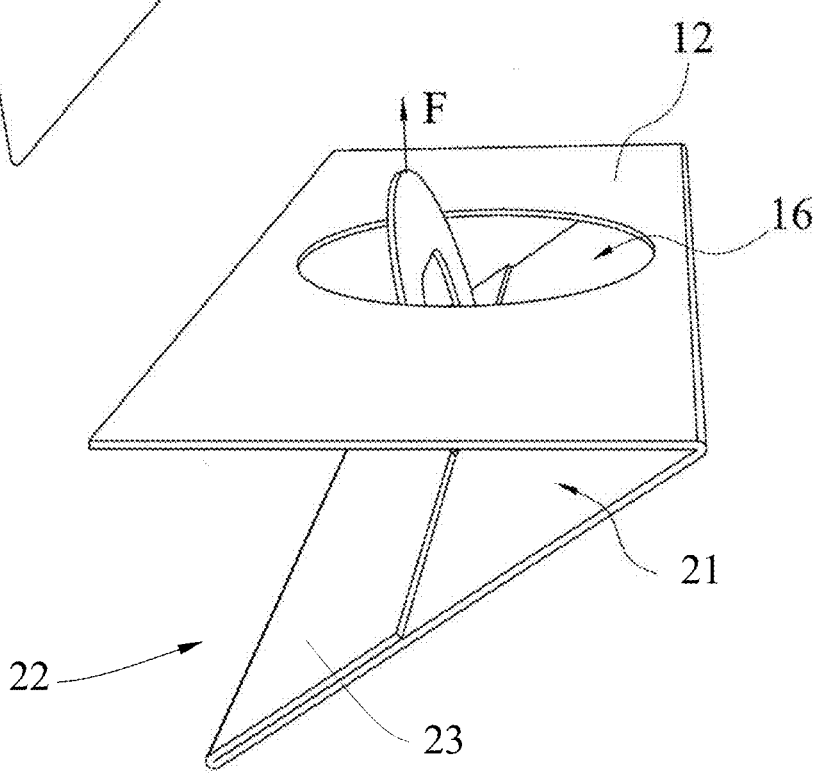
FIG. 6 illustrates a topside view of the inlet port assembly with the latch extending through the inlet opening of the port panel.
Figure 8:
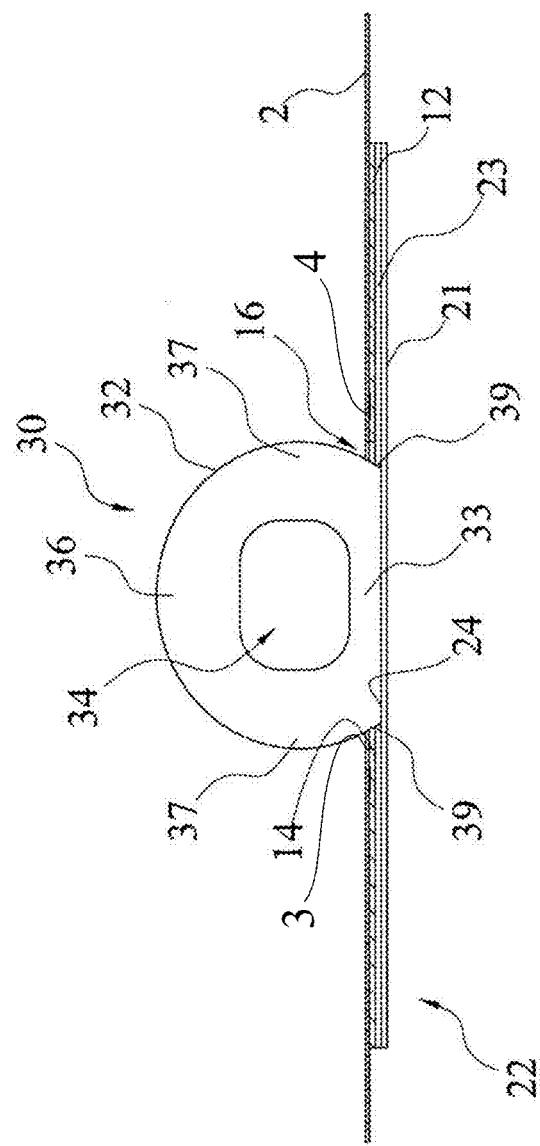
FIG. 8 shows a section view of the inlet port assembly of FIG. 7 in the closed, secured position, through line 8-8 of FIG. 7.

As shown in FIG. 2, to initiate a closure of the inlet opening 16, the latch 30 is folded outward, away from the closure panel 22, at the hinge 24, to expose the distal end 36 and the finger hole 34 of the latch 30. A person using the inlet port assembly 10 with a heating blanket 1 can reach a finger or two fingers (not shown) through the inlet opening 16, to grasp the latch 30 using distal end 36 and/or the finger hole 34, and apply a force F by pulling on the latch 30, as shown in FIG. 5, to pivot the closure panel 22 toward the port panel 12. As the latch 30 approaches the inlet opening 16 in the port panel 12, as shown in FIG. 6, the lateral ear portions 37 and distal end 36 of the latch 30 can be folded through the inlet opening 16 proximate the lateral centerline 100, and past the port rim 14, passing the latch 30 through the inlet opening 16, as shown in FIGS. 7 and 8, where the inwardly-tapered portions 39 of the neck 33 of the latch 30 wedge against the laterally-opposed portions 19 of the port rim 14 in the region 18, securing the closure panel 22 in the closed position.

Figure 9:
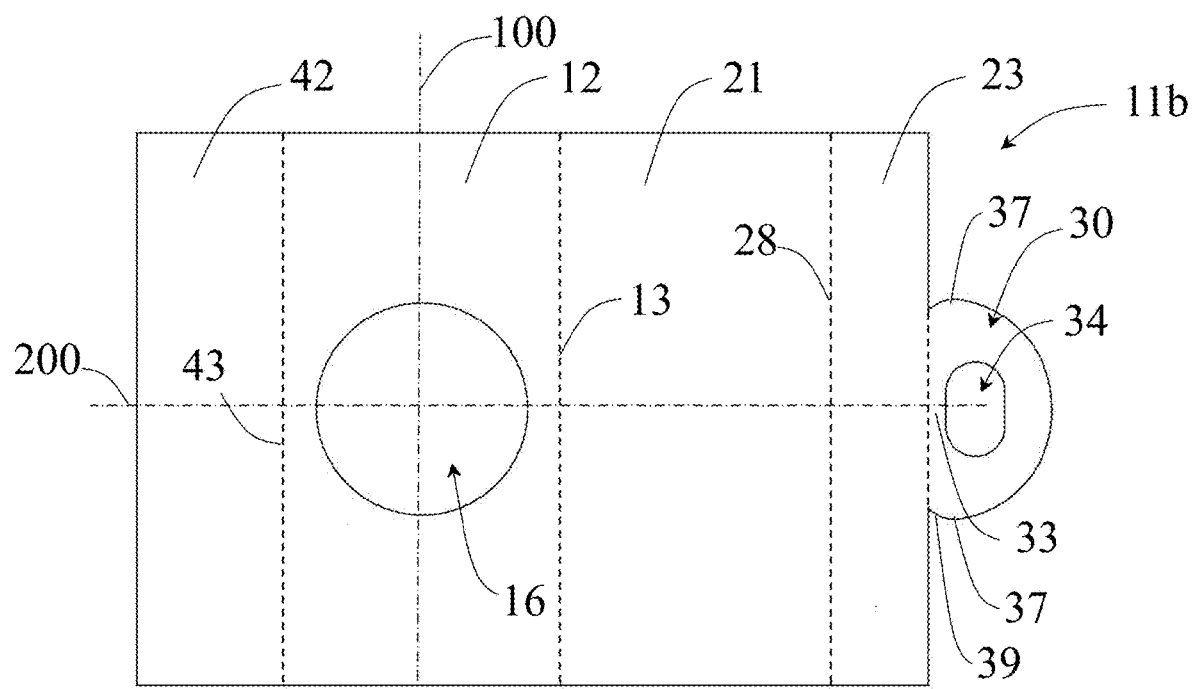
FIG. 9 shows a plan view of another embodiment of a blank to form a unitary inlet port assembly.
Figure 10:
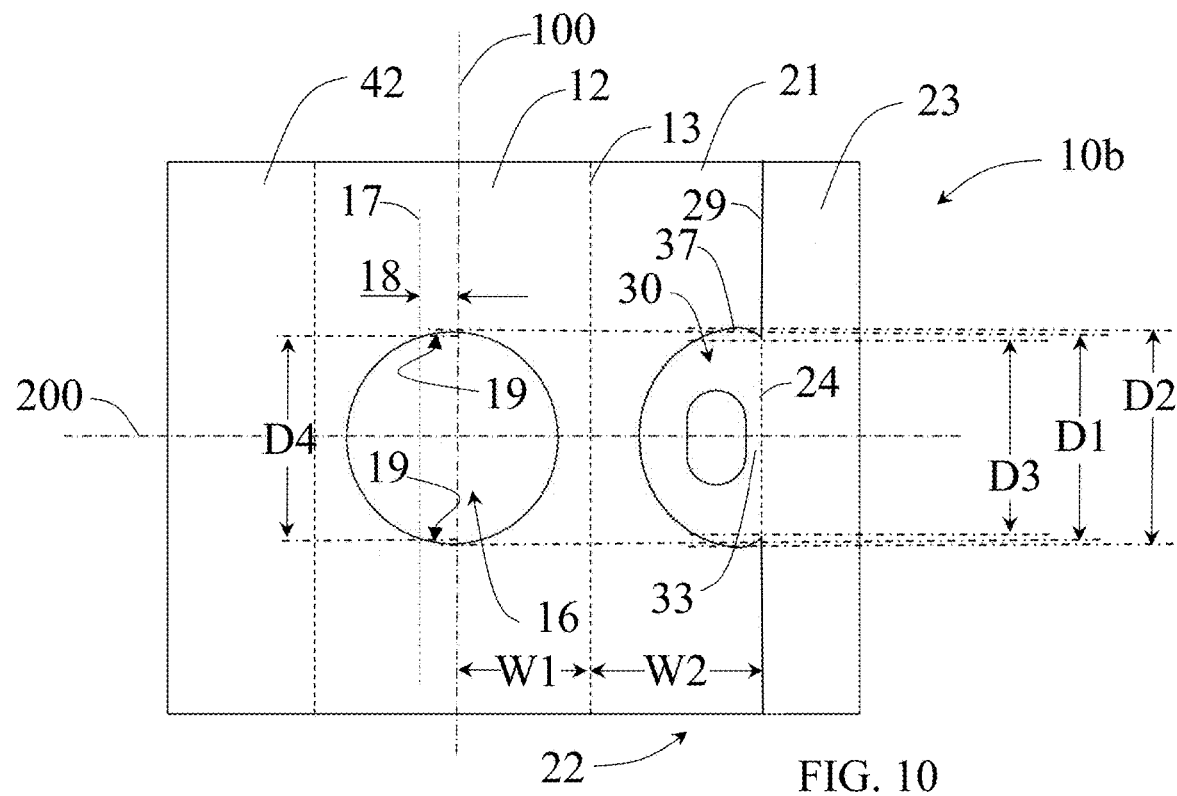
FIG. 10 shows a plan view of the blank of FIG. 9 formed into the unitary inlet port assembly.

Another embodiment of the present invention is shown in FIGS. 9 and 10, where features the same as those of the first embodiment are identified with similar reference numbers.

FIG. 9 shows a blank 6 that is formed out of a planar material, which forms the unitary inlet port assembly 7 after being folded and fixed as shown in FIG. 10. The blank 6 includes port panel 12, closure base 21, flap panel 23, and latch 30, which are similar to the same features of the first embodiment shown in FIGS. 3 and 4, though may have independently different dimensions and/or shapes. As shown in FIG. 10, the flap panel 23 is folded inwardly along the foldable joint 28, and is secured or fixed to the closure base 21 to form the closure panel 22, which is hingedly attached to the port panel 12 along the panel hinge 13.

In FIG. 10, the shaped opening 16 has a diameter D1. The neck 33 joining the latch 30 to the flap panel 23 has a length of D3, and the opposed lateral portions 37 or "ears" of the latch 30 have a span of a length of D2, greater than the length D3, and slightly larger than diameter D1 of the shaped opening 16. The length D3 of the neck 33 can be within a length range of a lateral chord length D4 between laterally-opposed portions 19 of the port rim 14 in the region 18. The lateral centerline 100 is disposed at a length W1 from the panel hinge 13 joining the port panel 12 and the closure panel 22, and the edge 29 of the folded-and-secured flap panel 23 is a length W2 from the panel hinge 13, where length W2 is greater than the length W1. When the closure panel 22 is folded over the port panel 12, the hinge 24 would be disposed along a lateral line 17 that defines the region 18 that defines a transverse chord of the circular inlet opening 16. By offsetting the hinge 24 from the lateral centerline 100 of the inlet opening 16 in the closed position, the lateral portions or "ears" 37 of the latch 30 can still pass with minimal clearance through the lateral center of the inlet opening 16, and when, as shown in FIG. 7, the latch 30 is un-folded on the outer side of the inlet opening 16, the opposing tapered portions 39 of the neck 33 of the latch 30 frictionally engage and wedge against the laterally-opposed portions 19 of the port rim 14 within the region 18, to better secure the closure panel 22 in the closed position.

In a particular embodiment of the blank 11, the lateral dimension (along lateral centerline 100) of the panels 42, 12, 21 and 23 are 5.88 inches (4.93 cm), with a broad tolerance, and the longitudinal dimensions (along longitudinal centerline 200) of the panels 42, 12, 21 and 23 are 1.03 inches (2.62 cm), 2.88 inches (7.32 cm), 2.94 inches (7.47 cm) and 1.56 inches (3.96 cm), respectively. The shaped opening has a diameter of 2.50 inches (6.35 cm) with a tolerance of 0.005 inches (0.01 cm). The latch 30 has a lateral width D2 of 2.31 inches (5.87 cm), longitudinal dimension, from the hinge 24 to the distal-most edge, of 1.31 inches (3.33 cm), and a neck 33 has a length D3 defining the hinge 24 of about 2.07 inches (5.26 cm). In general, the proportions between the dimensions D1, D2, D3, and the longitudinal dimensions of the panels 12, 21 and 23 are constant, although the absolute dimensions of each can vary. The latch 30 is laterally symmetrical, the shaped opening 16 is laterally and longitudinally symmetrical within the panel 12, and the latch 30 and the shaped opening 16 are aligned along the common longitudinal axis 200. The longitudinal axis 200, as well as the shaped opening 16 and the latch 30, can be symmetrical or asymmetrical within the footprint of the collective panels 42, 12, 21, and 23.

Figure 11:
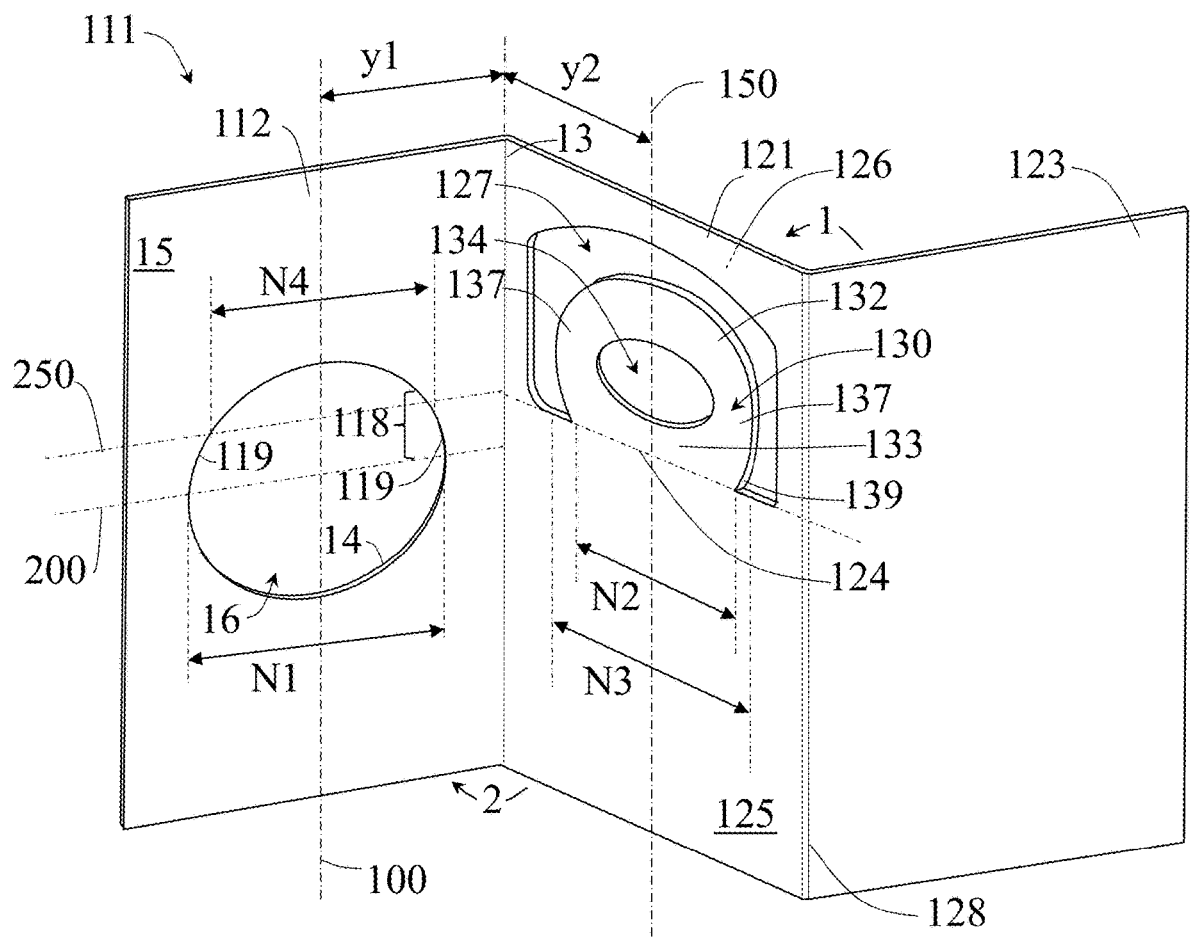
FIG. 11 shows a second embodiment of a blank for forming a unitary inlet port assembly that includes a port panel having an inlet opening, hinged to a closure panel having a transverse latch.

Another embodiment of the present invention is shown in FIGS. 11-14, where features the same as those of the first embodiment are identified with similar reference numbers. A blank 111 for a unitary inlet port assembly 110 is shown in FIG. 11 in a slightly folded position. The blank 111 includes a port panel 112 and a closure panel 122 hingedly attached to a side edge of the port panel 112 to form a panel hinge 13. The port panel 112 includes an inner face surface 15 that includes a port rim 14 that defines a shaped opening 16 formed through in a central portion of the port panel 112, forming an inlet opening 16.

The closure panel 122 includes a latch 130 attached to the closure panel 122 along a hinge 124. The hinge 124 extends transverse, or perpendicular, to the panel hinge 13, and when the closure panel 122 is folded against the port panel 112 in a closed position, shown in FIG. 12, the hinge 124 extends transverse (perpendicular) to a lateral centerline 100. The closure panel 122 provides a closure that covers the inlet opening 16 to form a port closure when folded to the closed position, shown in FIG. 14.

The latch 130 includes a tab having a circular or oval shape defined by an outer periphery 132. The outer edge 136 provides a place for a user to grasp the latch 130. A finger hole 134 can be formed in the body of the latch 130 to provide a catch for a finger of the user. The latch 130 includes a neck portion 133 that attaches to the closure panel 122 along the hinge 24, and opposed lateral portions 137 extend axially beyond the neck portion 133 and the ends of the hinge 124, and span a distance that is greater than the length of the hinge 124.

Figure 12:
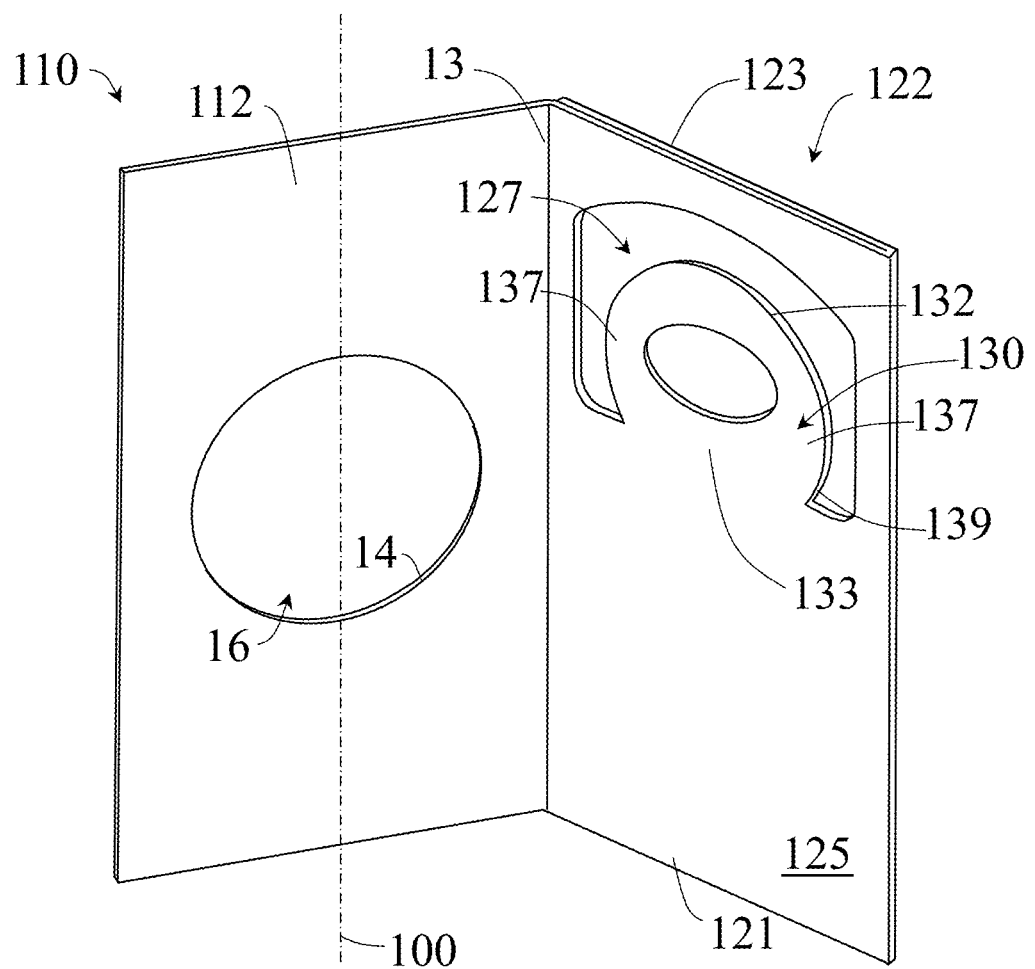
FIG. 12 shows the blank of FIG. 11 formed into the second embodiment of the unitary inlet port assembly.

FIG. 11 shows the blank 111 that is formed out of a planar material, and which forms the unitary inlet port assembly 110 after being folded and fixed as shown in FIG. 12. The blank 111 includes the port panel 112, a closure base 121 having a first side edge attached to the port panel 112 along a hinge joint 13, and a second side edge attached to a first edge of a flap panel 123 along a foldable joint 128. In the illustrated embodiment, the flap panel 123 has a second opposed edge 129. The closure base 121 comprises an outer surface 125 and has a shaped opening 127 formed as an inverted U-shape to form the latch 130, with the latch 130 attached to the closure base 121 along the hinge 124. The outer surface 125 of the closure base 121 completely surrounds the shaped opening 127 and the latch 130. The flap panel 123 is folded outwardly along the foldable joint 128, and is secured or fixed to an inside surface 126 of the closure base 121 to form the closure panel 122, which is hingedly attached to the port panel 112 along the panel hinge 13.

As noted, the outer surface 125 of the closure base 121 completely surrounds the shaped opening 127 and the latch 130, and likewise, the outer surface 125 would provide a close and consistent seal surface against the inside surface 15 of the port panel 112 that completely surrounds the inlet opening 16.

Figure 13:
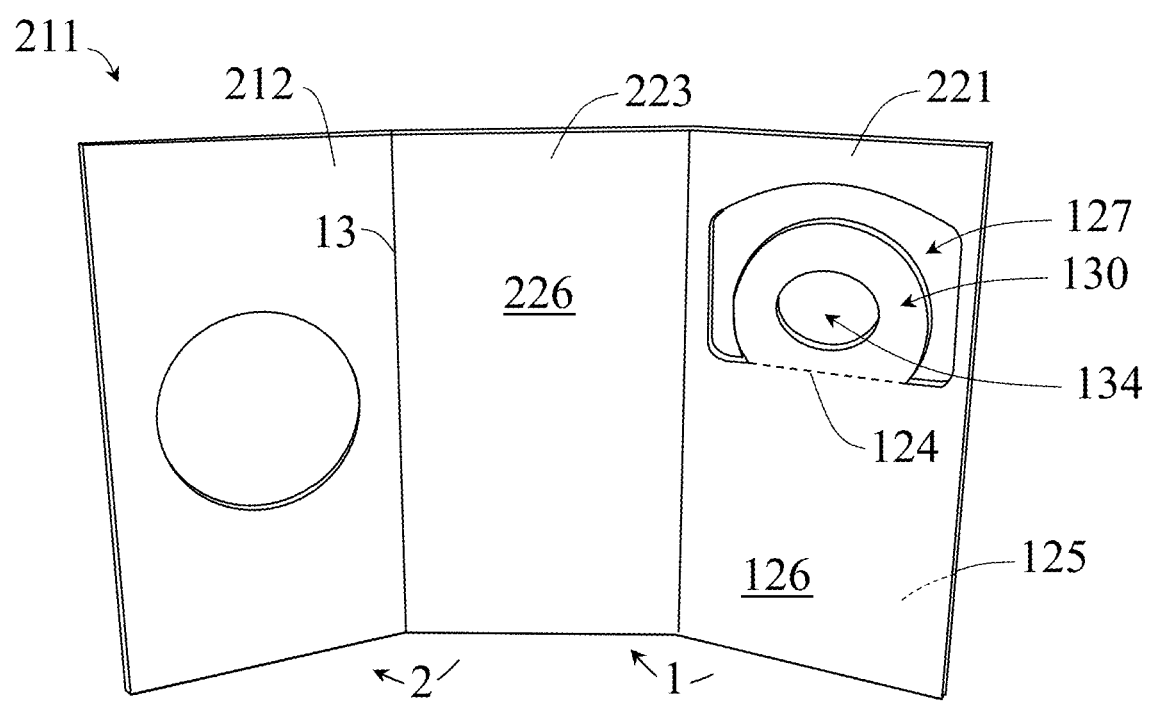
FIG. 13 illustrates an alternative blank of the second embodiment for forming the unitary inlet port assembly having a transverse latch.

FIG. 13 shows an alternative embodiment of a blank 211 that is formed out of a planar material and formed into a unitary inlet port assembly substantially the same as inlet port assembly 110. The blank 211 includes the port panel 212 substantially the same as the port panel 112 of the second embodiment; a flap panel 223, substantially the same as the flap panel 123 of the second embodiment, having a first edge attached to the port panel 212 along a hinge joint 13, and a opposed second edge; and a closure base 221 having a first side edge attached to the flap panel 223 along a foldable joint 28. The closure base 221 is substantially the same as the closure base 121 of the second embodiment, comprising a body panel having the outer surface 125 with the shaped opening 127 to form the latch 130 attached to the body panel along the axially-oriented hinge 124. The closure base 221 is folded inwardly along the foldable joint 28, and is secured or fixed to an inside surface 226 of the flap panel 223 to form the closure panel 222, which is hingedly attached to the port panel 212 along the panel hinge 13.

In FIG. 11, the inlet opening 16 has an open area having an axial length D1, and in the illustrated embodiment, a largest axial dimension N1 along the axial centerline 200, illustrated as a circle with a diameter N1. The axially-opposed portions 119 of the port rim 14 in the region 118 define a range of chord lengths there between, including a chord length N4 disposed along axial line 250.

On the closure panel 122, the neck 133 joins the latch 130 to the flap panel 123 along the hinge 124 having a length of N2, and the opposed ear portions 137 of the latch 130 have a span of a length of N3, greater than the length N2. To allow the latch 130 to pass through the inlet opening 16 without significant interference, the span length N3 of the ears portion 137 of the latch 130 is the same or less than the largest axial dimension N1 of the inlet opening 16. Further, the length N2 of the neck 133 is within a length range of an axial chord length N4 between the axially-opposed portions 119 of the port rim 14 in the region 118.

The lateral centerline 100 is at a distance y1 from the panel hinge 13 that joins the port panel 112 and the closure panel 122, while the lateral centerline 150 through the latch 130 in the closure base 121 is at a distance y2 from the panel hinge 13. In another embodiment, length y1 and y2 are the same, or only of slight difference, such that the latch 130 in the closed position is centered within the inlet opening 16.

Figure 14:
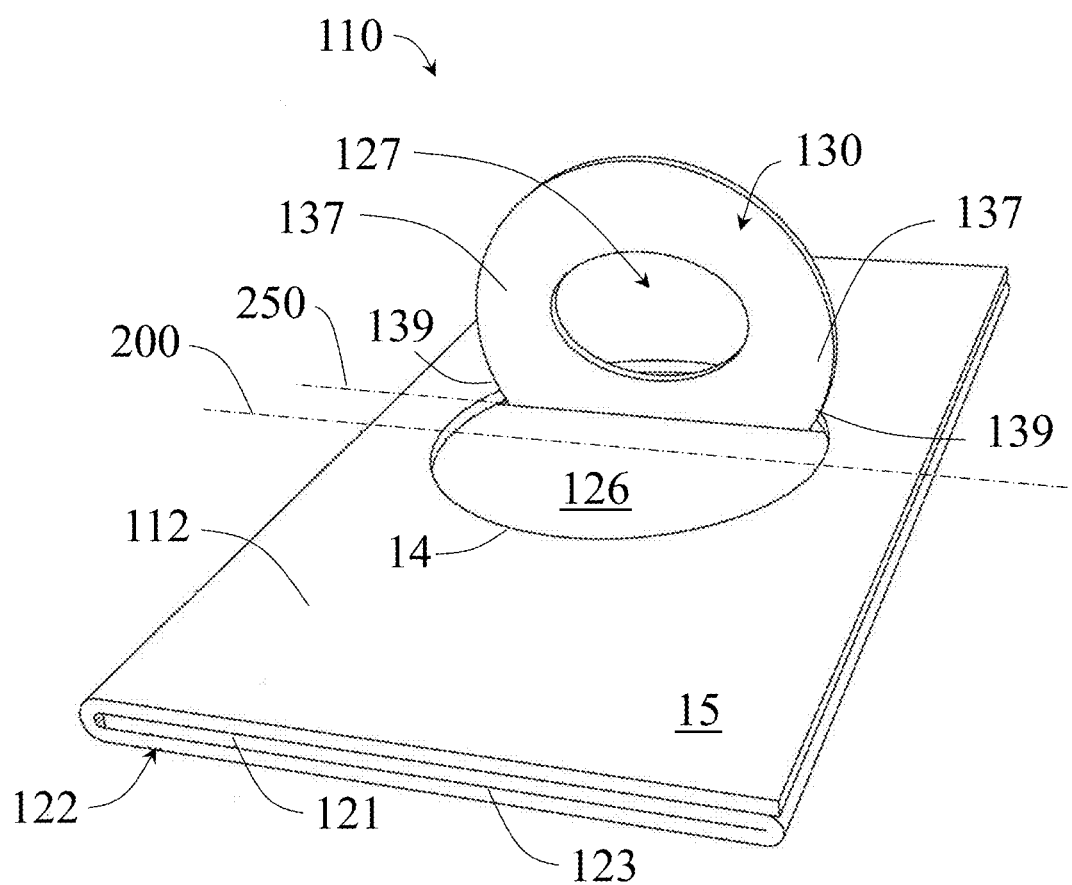
FIG. 14 illustrates a topside view of the unitary inlet port assembly of FIG. 12 with the closure panel pulled into a closed position against the port panel, and the transverse latch pulled through the inlet opening into a secured position against the rim of the inlet opening.

In the illustrated embodiment, the hinge 124 is disposed along an axial line 250, such that when the closure panel 122 is folded to the closed position, the hinge 124 is disposed along the same axial line 250 within the region 118 and defines a chord line of the circular inlet opening 16. By off-setting the hinge 124 along axial line 250 from the axial centerline 200 of the inlet opening 16, the opposed ear portions 137 of the latch 130 can be folded to pass with minimal clearance through the axial center of the inlet opening 16, and when, as shown in FIG. 14, the latch 130 is un-folded on the outer side of the inlet opening 16, the opposing tapered portions 139 of the neck 133 of the latch 130 frictionally engage and wedge against the axially-opposed portions 119 of the port rim 14 in the region 118, to better secure the closure panel 122 in the closed position.

To initiate a closure of the air inlet port, the latch 130 of the closure panel 122 is folded outward and away from the closure panel 122, at the hinge 124, to expose the distal end 136 and/or finger hole 134 of the latch 130. A person using the inlet port assembly 10 with a heating blanket can reach a finger or two fingers through the inlet opening 16, to grasp the latch 130 using the finger hole 134, and apply a force by pulling on the latch 130 to pivot the closure panel 122 toward the port panel 112, toward a closed position. As the latch 130 approaches the inlet opening 16 in the port panel 112, the opposed ear portions 137 of the latch 130 can be folded through the inlet opening 16 proximate the longitudinal centerline 200, and past the port rim 14, to pass the latch 130 through the inlet opening 16 to the outer side of the port panel 112, as shown in FIG. 14, where the inwardly-tapered portions 139 of the neck 133 of the latch 130 wedge against the axially-opposed portions of the port rim 14 in the region 118, securing the closure panel 122 in the closed position against the port panel 112.

In another embodiment, the length N2 of the neck 133 can be the same or slightly shorter than the length of the largest axial dimension N1, and the opposed ear portions 137 of the latch 130 have a span of a length of N3 greater than the length N2 and N1. To allow the latch 130 to pass through the inlet opening 16, the opposed ear portions 137 of the latch 130 can be rolled or curled inwardly, around the lateral centerline 150 through the latch 130, and pulled through the inlet opening 16.

In an alternative to the second embodiment, a span of the opposed ear portions 137 of the latch 130 can extend as wide as or wider than the corresponding diameter or maximum dimension of the inlet opening 16. In this embodiment, to pass the latch 130 up and through the inlet opening 16, the user can curl the opposed ear portions 137 around the center axis 150 of the latch 130, to pass the latch 130 through the inlet opening 16. In this alternative embodiment, the hinge 124 of the latch 130 in the closure panel 122 can be positioned along axial line 250 to register co-axially to the axial centerline 200 of the inlet opening 16, in the closed position, though can also be slightly off-set therefrom. This alternative embodiment would require more dexterity from a user, but also provides a secure configuration on the part of the closure panel 122 in the closed position.

Figure 15:
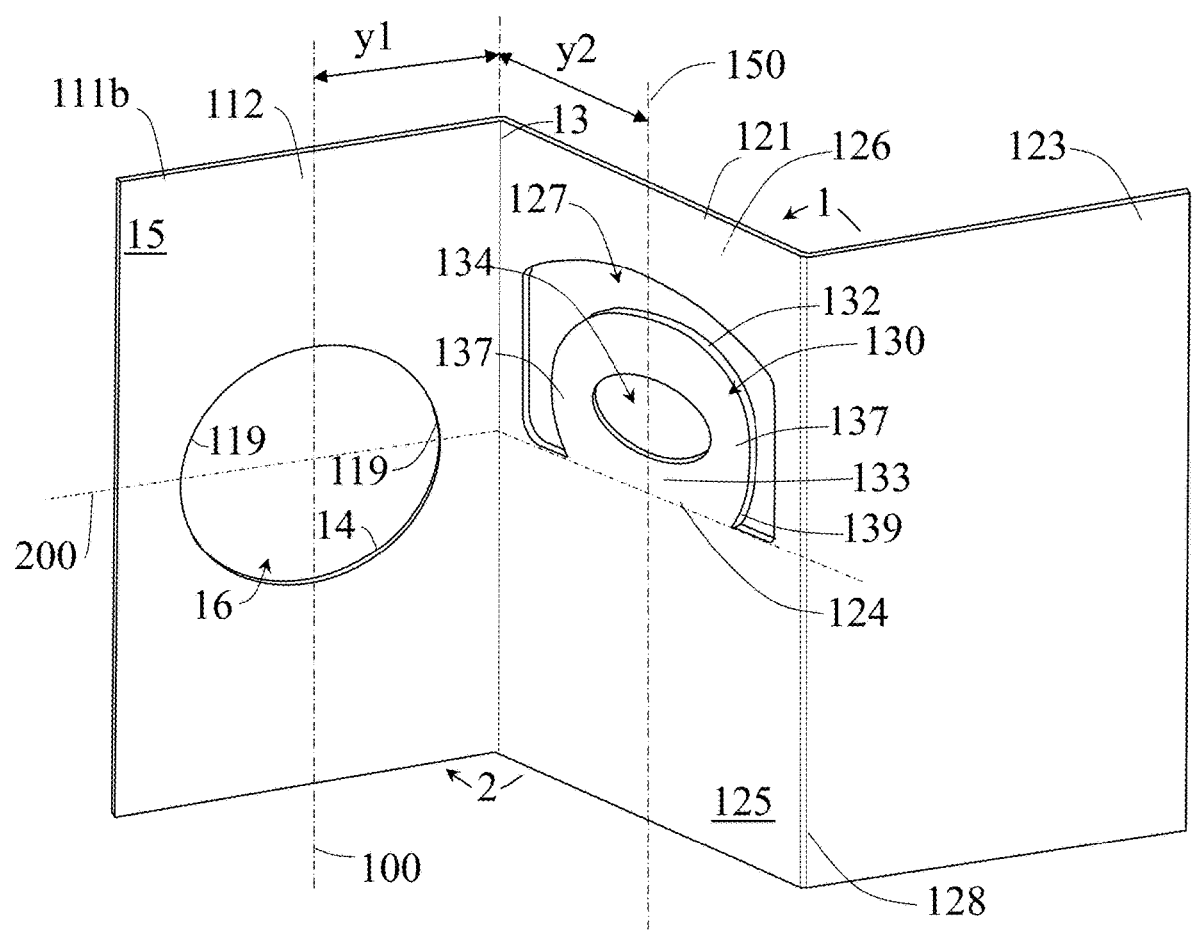
FIG. 15 shows an alternative embodiment of the blank of FIG. 11, with the latch positioned along a fold line that aligns with the longitudinal centerline of the port opening.
Figure 16:
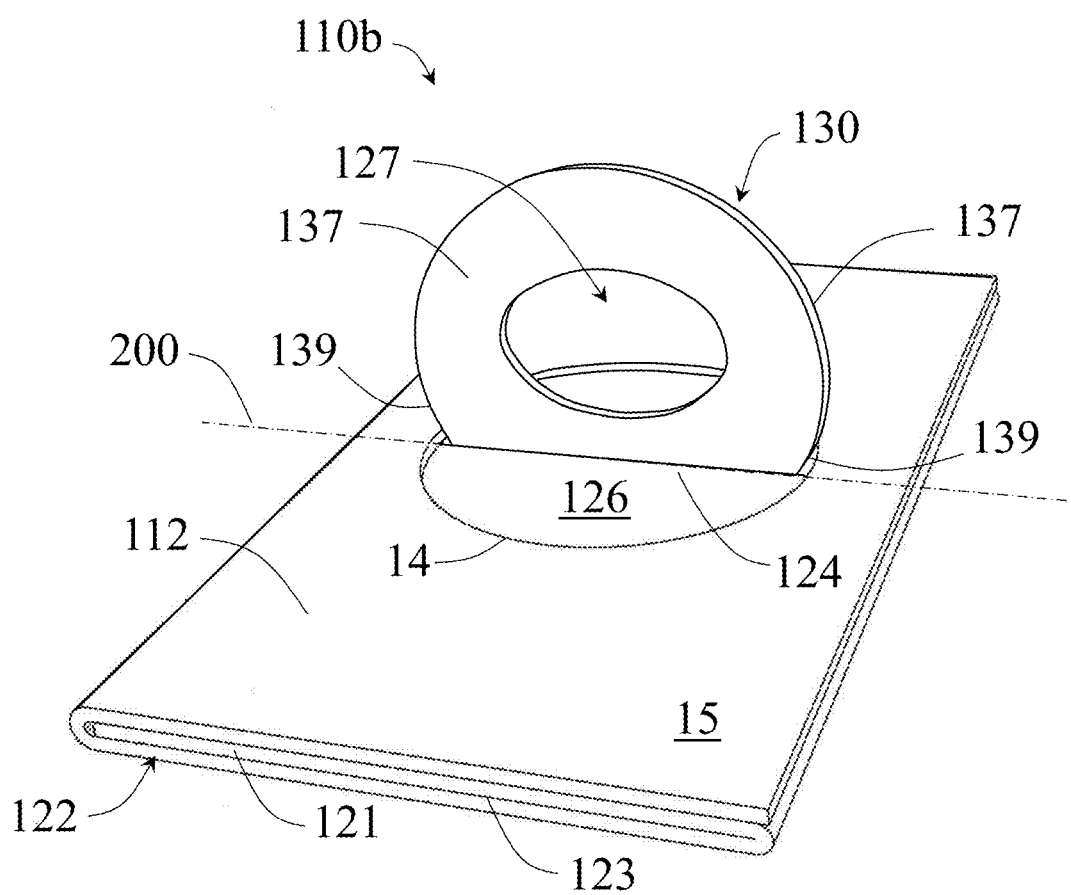
FIG. 16 illustrates a topside view of the unitary inlet port assembly of FIG. 15 with the closure panel pulled into a closed position against the port panel, and the transverse latch pulled through the inlet opening into a secured position against the rim of the inlet opening.

Another embodiment of a blank of the present invention is shown in FIG. 15 which illustrates the port panel being adjacent to the closure panel having the latch. FIG. 15 shows an alternative embodiment of a blank 111b that is similar to the embodiment of the blank 111 described and shown in FIG. 11. The blank 111b is formed out of a planar material that is rectangular in shape, and can be folded and fixed into a unitary inlet port assembly similar to the assembly 110 as shown in FIG. 14, except with respect to the positioning of the latch 130 to position the hinge 124 along and aligned with the longitudinal centerline 200. The latch 130 of the embodiment shown in FIG. 15 otherwise functions in the same manner to form the closure as shown in FIG. 16.

Figure 17:
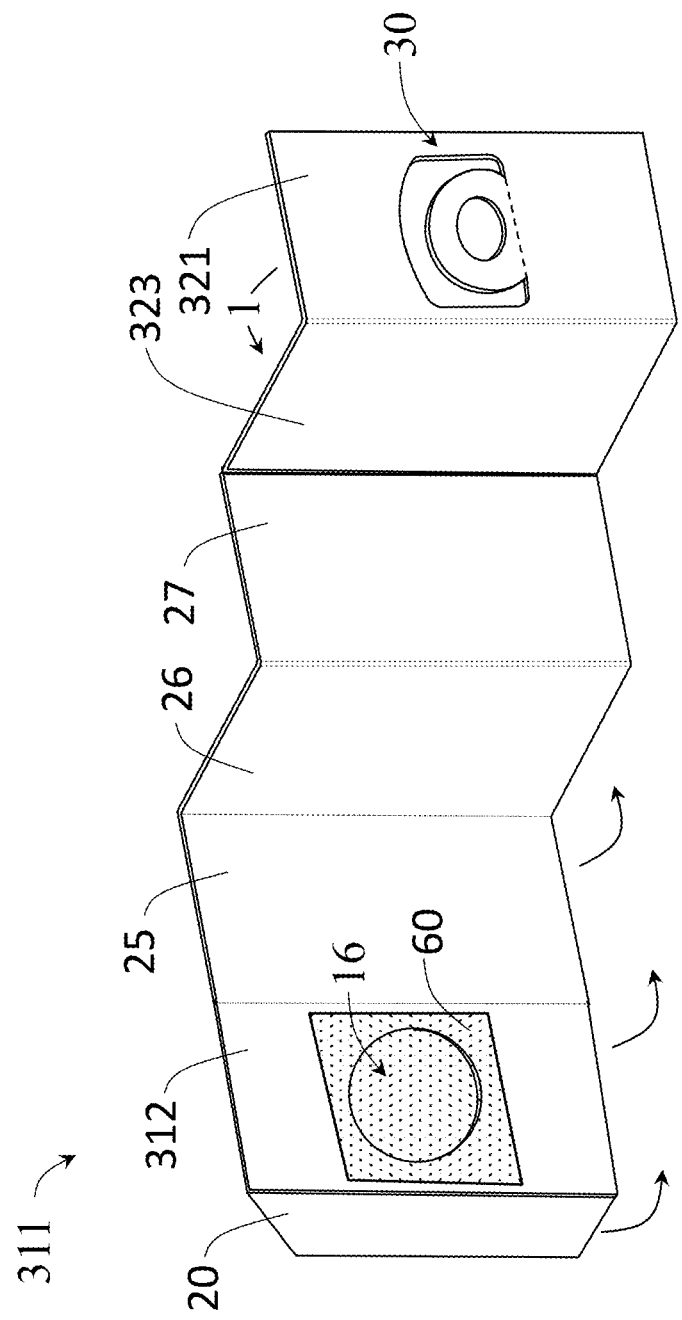
FIG. 17 shows a plan view of a blank of alternative embodiment of a multi-walled inlet port assembly as shown in FIG. 18.
Figure 18:
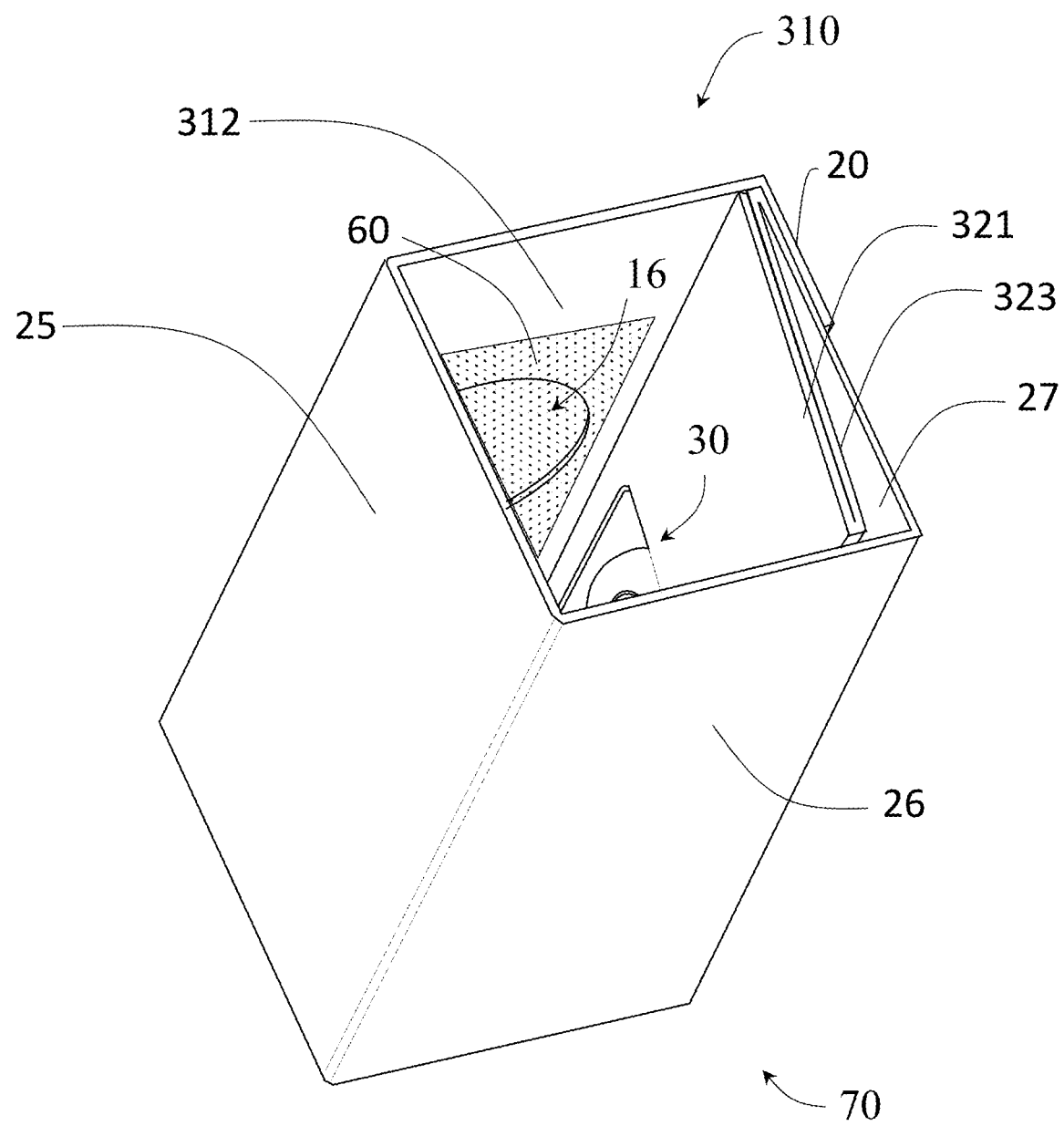
FIG. 18 shows the blank of FIG. 17 formed into the multi-walled inlet port assembly.

In another embodiment of the invention, the unitary inlet port assembly can be formed as a tubular member having the air inlet port. FIGS. 17-18 show a blank 311 formed out of a planar material that is rectangular in shape and includes a series of adjoined panels that can be folded and secured into a tubular member 70. The series of panels include the port panel 312 at one end of the series, and a closure panel 321 and flap panel 323 at the opposite end. Three intermediate panels 25, 26 and 27 form three of the sides of the tubular member 70. An end panel 20 extending from the port panel 312 is used to secure the port panel 312 to the intermediate panel 27 and thereby to secure the series of panels into the tubular member 70. The end panel 20 may overlap and be secured to the intermediate panel by an adhesive. The closure panel 321 and flap panel 323 are hinged at the joint of the closure panel 312 with the intermediate panel 27, extending within the interior of the tubular member 70 and pivotable to provide for the closure of the opening 16 of the port panel 312.

In an embodiment of the invention, the unitary inlet port assembly can include a temporary covering attached over the port opening 16. In one embodiment, the temporary covering is a frangible covering comprising a tissue paper that prevents dust or other debris from entering into the port opening 16 during storage. As illustrated in FIGS. 17 and 18, the tissue paper 60 can be placed and secured, typically with an adhesive material, on the inside surface of the port panel 12, covering the port opening 16. Prior to use, the user can insert a finger into the port opening 16 to puncture and/or grasp the tissue material 60 for removal.

Figure 19:
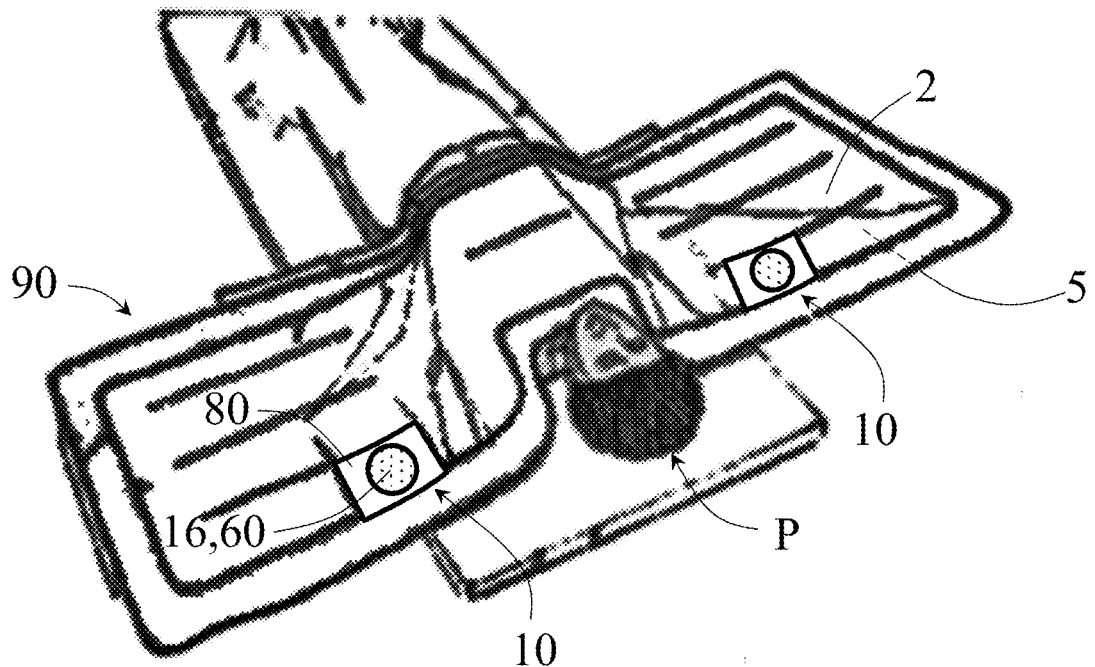
FIG. 19 illustrates a heating blanket in a position covering a patient, including one or more of the inlet port assembly.

The inlet port assembly 10 is adapted for mounting on an inflatable device illustrated in FIG. 19 as a patient warming blanket 90, covering a patient P. Other non-limiting examples of an inflatable device include a patient warming gown. One or more, though typically at least two, inlet port assemblies 10, can be installed into the patient warming blanket 90. The inlet opening 16 has a shape and a structure for engaging and retaining an inlet air nozzle 92 of a warm air hose 94 through which warm air WA can pass to inflate the inflatable device 90. When not engaged by an air hose nozzle 92, the inlet opening 16 of the port panel 12 of the inlet port assembly 10 can be closed, blocked, or sealed with the closure panel 22. The closure panel 22, folded into the closed position, blocks the inlet opening 16 of the port panel 12 in order to inhibit, restrict or prevent air escaping the inflatable device 90 when being inflated with warm air through an inlet opening of one of the other inlet port assemblies 10.

The patient warming blanket 90 can also include variations in its manner of placement upon the patient P. These variations can depend upon the needs of a given situation and non-limiting examples include the blanket 90 being placed transversely upon the patient with the inlet opening 16 being closer to the patient's P head as shown in FIG. 19. The warming blanket 90 can also be placed upon a prior blanket that has been placed upon the patient P as again shown in FIG. 19. The inlet port assembly 10 can also be designed to be placed in the blanket 90 that is conveniently accessible to hospital and clinic personnel. Non-limiting examples of placement of the inlet port assembly 10 near the head of the patient P as shown in FIG. 19. The inlet port assembly 10 can be fixed in the warming blanket 90 such that when in use, the port panel 12 of the inlet port assembly 10 is oriented horizontally, perpendicularly, or angularly, to the surface of the operating table upon which a patient P may lie, so as to operate the inflation and deflation mechanism in a manner that is convenient and efficient for the hospital and clinic personnel, and causes little or no discomfort to the patient P.

A heating blanket 90 can include an outer, air-impervious film material 2 and an inner, patient-facing, air-pervious nonwoven or woven fabric or film material 5, which are joined along respective peripheries and along interior bonded seems to define an internal baffled cavity. Examples of warming blankets are described in U.S. Pat. Nos. 4,572,188 and 5,405,371, the disclosures of which are incorporated by reference in their entireties. When warm air is dispensed into the blanket through the inlet opening, the interior cavity of the blanket 90 expands, and vents a controlled, uniform flow of air through the patient-facing, air-pervious nonwoven or woven fabric or film material 5, to warm the patient.

Typically, the inlet port assembly, including any of the inlet port assemblies described herein, the illustrated herein as port assembly 10, is installed into the outer, air-impervious film material 2. In one embodiment, illustrated in FIG. 7, the outer, air-impervious film material 2 has a circular opening defined by a rim 3, and an inlet port assembly 10 positioned on the inside surface of the air-impervious film material 2 with the port opening 16 registered with the circular opening of the air-impervious film material 2. A seal 4 can be formed between the air-impervious film material 2 and the port panel 12, radially outside the opening 16, using adhesive or ultrasonic bonding. In other embodiments, the tubular inlet port can include any of the other embodiments of the unitary inlet port assembly described herein.

In another embodiment illustrated in FIG. 21, a shaped opening is formed in the outer, air-impervious film material 2 to facilitate inserting and positioning the inlet port assembly 10. The shaped opening is illustrated as a rectangular opening 40, the opening 40 having the same dimensions as the port panel 12 of the inlet port assembly 10. An adhesive sealing film 50 is used to secure and seal the inlet port assembly 10 to the outer air-impervious film material 2. An adhesive sealing film 50 includes an upper surface on which user information and graphics can be printed, and an underside that includes an adhesive material. As shown in FIGS. 21 and 22, the adhesive sealing film 50 has a port opening 51 defined by an edge 52 that is configured and assembled to register and align with the port opening 16 of the inlet port assembly 10. The adhesive sealing film 50 has a periphery that provides a footprint that encompasses the opening 40 in the air-impervious film material 2. An outer seal zone 54 on the adhesive underside, along the periphery of the adhesive sealing film 50, adheres securely to and forms a seal with a seal zone 41 surrounding and encompassing the opening 40 of the air-impervious film material 2. An inner seal zone 55 on the adhesive underside and surrounding the port opening 51 of the adhesive sealing film 50, adheres securely to and forms a seal with the upper-facing surface 15 of the port panel 12 of the inlet port assembly 10, and thereby securing and sealing the inlet port assembly 10 to the outer air-impervious film material 2.

Figure 23:
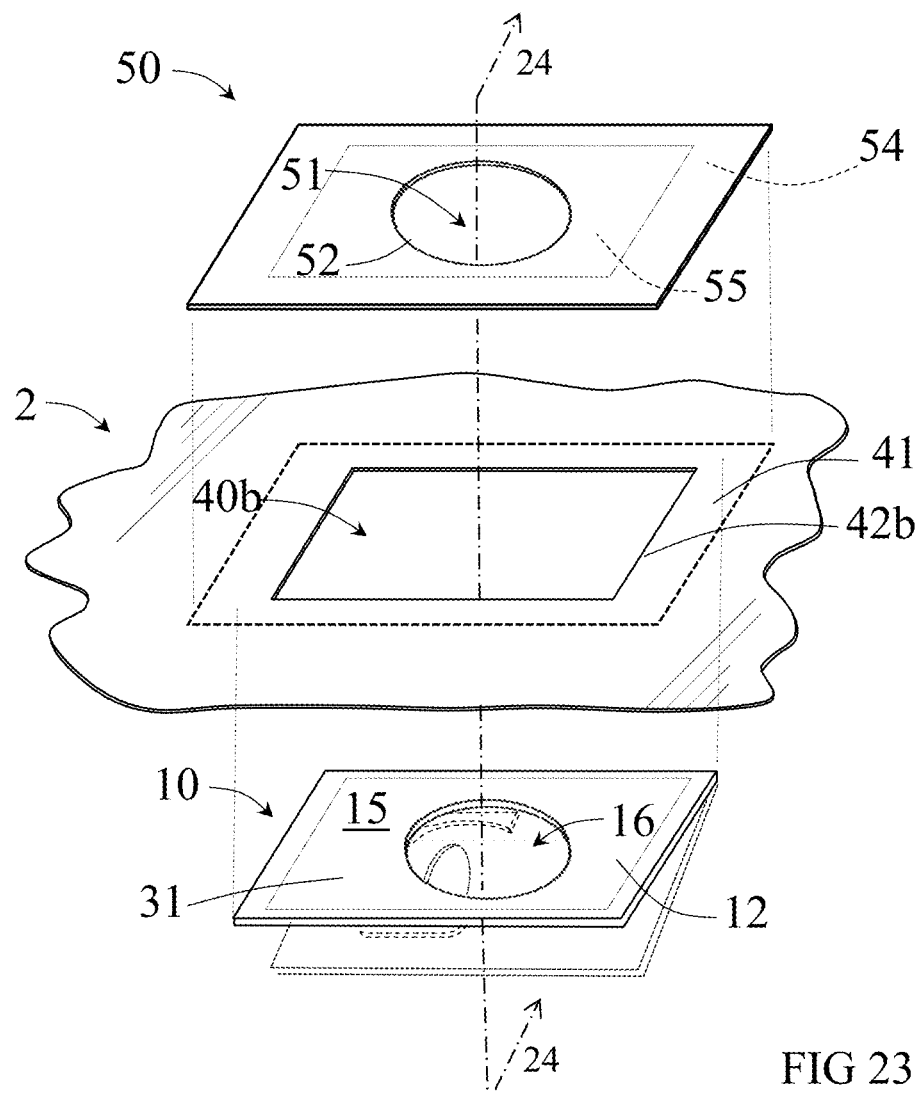
Figure 24:
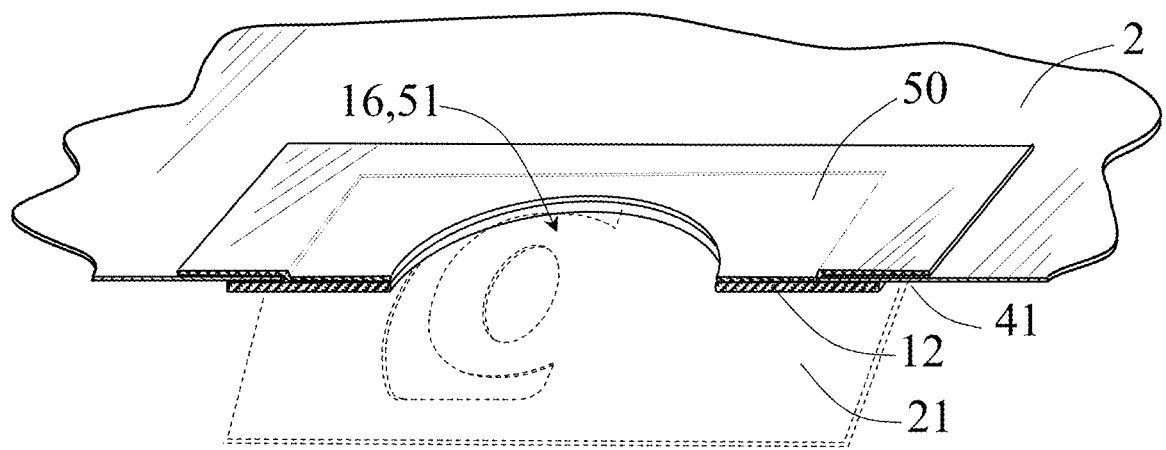

In an embodiment illustrated in FIGS. 23 and 24, the outer, air-impervious film material 2 has a similar rectangular opening 40b having dimensions in length and width that are smaller than the dimensions in length and width of the port panel 12 of the inlet port assembly 10, such that the port panel 12 of the inlet port assembly 10 completely covers the underside of the opening 40 of the air-impervious film material 2. The adhesive sealing film 50 has a similar port opening 51 to register and align with the port opening 16 of the inlet port assembly 10. An outer seal zone 54 on the adhesive underside and around the periphery of the adhesive sealing film 50, adheres securely to and forms a seal with a seal zone 41 on the upper surface surrounding the opening 40 of the air-impervious film material 2, while the inner seal zone 55 on the adhesive underside and surrounding the port opening 51 of the adhesive sealing film 50, adheres securely to and forms a seal with an inner seal zone 31 on the upper-facing surface 15 of the port panel 12 of the inlet port assembly 10, and thereby securing and sealing the inlet port assembly 10 to the outer air-impervious film material 2.

In an embodiment of the invention, the material of the inlet port assembly 10, 110, or 210, or the blanks 11, 111 or 211, or the adhesive sealing film 50 is a generally flexible, resilient sheet of material, such as plastic or a wood pulp product, such as paper or cardboard. The material is preferably die-cut into the desired shape. Alternatively, the material may be stamped, extruded, molded or otherwise formed into the desired shape.

Accordingly, it is to be understood that the invention is not to be limited by the specific illustrated embodiment, but only by the scope of the appended claims.

We claim:

1. A unitary inlet port assembly for use as a closable air inlet port for an inflatable heating blanket or garment, including:
    a) a port panel associated with an outside layer of the inflatable heating blanket or garment, the port panel including a first side edge, an inside surface, and an annular rim defining an inlet opening through the port panel that is configured for receiving an air hose nozzle; and
    b) a closure panel that is configured to pivot between an open position and a closed position relative to the port panel, and disposed within an interior portion of the inflatable heating blanket or garment, the closure panel including an outer-facing surface, and a side edge that forms a panel hinge with the first side edge of the port panel, and
    c) a latch extending from and positioned on the outer-facing surface of the closure panel to register with the inlet opening of the port panel when the closure panel is pivoted to the closed position at which the outer-facing surface of the closure panel confronts and engages the inside surface of the port panel, and where the latch is configured to engage the annular rim of the port panel to hold the closure panel in the closed position.

2. The unitary inlet port assembly according to claim 1, wherein the annular rim is circular to form a circular inlet opening.

3. The unitary inlet port assembly according to claim 2, wherein the latch is attached hingedly to the outer-facing surface of the closure panel.

4. The unitary inlet port assembly according to claim 3, wherein the latch comprises a circular or oval tab, including a neck portion that forms a hinge with the outer-facing surface of the closure panel, and two opposed lateral portions of the latch that extend laterally beyond the neck.

5. The unitary inlet port assembly according to claim 4, wherein a periphery of the two opposed lateral portions of the latch span a distance that is the same distance or less than the diameter or maximum dimension of the inlet opening.

6. The unitary inlet port assembly according to claim 5, wherein the hinge of the latch extends along a latch hinge line that is parallel with the panel hinge.

7. The unitary inlet port assembly according to claim 6, wherein the latch hinge line, when the closure panel is folded into the closed position, defines a chord line of the inlet opening that is off-set from the lateral centerline of the inlet opening.

8. The unitary inlet port assembly according to claim 5, wherein the hinge of the latch extends along a latch hinge line that is perpendicular to the panel hinge.

9. The unitary inlet port assembly according to claim 8, wherein the latch hinge line, when the closure panel is folded into the closed position, defines a chord line of the inlet opening that is off-set from the longitudinal centerline of the inlet opening.

10. The unitary inlet port assembly according to claim 1, wherein the latch comprises a circular or oval tab, including a neck portion that forms a hinge with the outer-facing surface of the closure panel, and two opposed lateral portions of the latch that extend laterally beyond the neck.

11. The unitary inlet port assembly according to claim 10 wherein a periphery of the two opposed lateral portions of the latch span a distance that is the same distance or less than the diameter or maximum dimension of the inlet opening.

12. The unitary inlet port assembly according to claim 10, wherein the hinge of the latch extends along a latch hinge line that is parallel with the panel hinge.

13. The unitary inlet port assembly according to claim 12, wherein the latch hinge line, when the closure panel is folded into the closed position, defines a chord line of the inlet opening that is off-set from the lateral centerline of the inlet opening.

14. The unitary inlet port assembly according to claim 10, wherein the hinge of the latch extends along a latch hinge line that is perpendicular to the panel hinge.

15. The unitary inlet port assembly according to claim 14, wherein the latch hinge line, when the closure panel is folded into the closed position, defines a chord line of the inlet opening that is off-set from the longitudinal centerline of the inlet opening.

16. The unitary inlet port assembly according to claim 1, wherein unitary inlet port assembly is formed by folding a cardboard blank material.

17. The unitary inlet port assembly according to claim 1, further including a temporary covering attached releasably over the port opening, the temporary covering comprising a tissue paper that prevents dust or other debris from entering into the port opening during storage.

18. The unitary inlet port assembly according to claim 1, wherein the port panel is a panel portion of a tubular member that is disposed within a tubular section of the interior portion of the inflatable heating blanket or garment.

19. The unitary inlet port assembly according to claim 18, wherein the tubular member further includes at least two additional panels, including a first panel that includes a side edge that forms a second panel hinge with said side edge of the port panel, a second panel that includes a side edge that forms a third panel hinge with an opposed side edge of the port panel.

20. The unitary inlet port assembly according to claim 19, further including a third panel that includes a first side edge that forms a fourth panel hinge with an opposed side edge of the first panel, and a second side edge that forms a fifth panel hinge with an opposed side edge of the second panel, wherein the tubular member forms a rectangular cylinder.

21. The unitary inlet port assembly according to claim 19, further including an adhesive sealing film that secures and seals the inlet port assembly to an outer air-impervious film material of the inflatable heating blanket or garment.

\* \* \* \* \*